US006552346B2

(12) United States Patent
Verbinski et al.

(10) Patent No.: US 6,552,346 B2
(45) Date of Patent: *Apr. 22, 2003

(54) DENSITY DETECTION USING DISCRETE PHOTON COUNTING

(75) Inventors: Victor V. Verbinski, La Jolla, CA (US); Scott T. Smith, San Diego, CA (US); Kenneth H. Valentine, San Diego, CA (US); Victor J. Orphan, Leucadia, CA (US)

(73) Assignee: Science Applications International Corporation, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/834,377

(22) Filed: Apr. 12, 2001

(65) Prior Publication Data

US 2001/0020682 A1 Sep. 13, 2001

Related U.S. Application Data

(63) Continuation of application No. 09/398,980, filed on Sep. 17, 1999, now Pat. No. 6,255,654, which is a continuation of application No. 08/921,854, filed on Sep. 2, 1997, now abandoned, which is a continuation of application No. 08/546,999, filed on Oct. 23, 1995, now abandoned.

(51) Int. Cl.[7] .............................................. G01N 23/10
(52) U.S. Cl. ............................. 250/358.1; 250/360.1; 378/57; 378/198
(58) Field of Search ................................. 250/358.1, 360.1, 250/359.1, 370.11; 378/57, 198, 197, 51, 54, 55

(56) References Cited

U.S. PATENT DOCUMENTS

| 3,124,679 A | | 3/1964 | Tittman et al. |
| 3,780,291 A | | 12/1973 | Stein et al. |
| 3,790,785 A | * | 2/1974 | Paolini et al. ............... 250/363 |
| 3,808,444 A | | 4/1974 | Schneeberger et al. |
| 3,835,324 A | | 9/1974 | Weigle |
| 3,997,787 A | | 12/1976 | Fearon et al. |
| 4,064,440 A | * | 12/1977 | Roder ........................ 250/369 |
| 4,229,654 A | | 10/1980 | Arya et al. |
| 4,251,726 A | | 2/1981 | Alvarez |
| 4,430,568 A | * | 2/1984 | Yoshida et al. .......... 250/358.1 |
| 4,598,202 A | * | 7/1986 | Koechner .................... 250/366 |
| 4,599,740 A | * | 7/1986 | Cable .......................... 378/57 |

(List continued on next page.)

FOREIGN PATENT DOCUMENTS

| GB | 2277013 A | 10/1994 |

OTHER PUBLICATIONS

"Industrial X–Ray Units," trade brochure General Electric X–Ray Corporation, Pub. 7A–700.

U.S. application Ser. No. 09/398,980, titled "Density Detection using Discrete Photon Counting," filed Sep. 17, 1999, relied on under 35 U.S.C. §120.

U.S. application Ser. No. 08/921,854, titled "Density Detection using Discrete Photon Counting," filed Sep. 2, 1997 (now abandoned), relied on under 35 U.S.C. §120.

(List continued on next page.)

Primary Examiner—Constantine Hannaher
Assistant Examiner—Albert Gagliardi
(74) Attorney, Agent, or Firm—Kilpatrick Stockton LLP

(57) ABSTRACT

A system and method of density detection in a target object involve irradiating the target object, detecting a first and second discrete number of photons penetrating the target object through respective first and second prescribed volumes and entering respective first and second radiation detectors. First and second numbers of photons detected by the first and second radiation detectors are counted, and a display output signal is generated in response to the first and second numbers. A graphical representation of the densities within the first and second volumes of the target object is displayed.

20 Claims, 44 Drawing Sheets

U.S. PATENT DOCUMENTS

| | | | |
|---|---|---|---|
| 4,697,594 A | | 10/1987 | Mayo, Jr. |
| 4,893,015 A | * | 1/1990 | Kubierschky et al. ...... 250/369 |
| 4,973,846 A | | 11/1990 | Lanza et al. |
| 5,091,924 A | * | 2/1992 | Bermbach et al. ............ 378/57 |
| 5,151,588 A | * | 9/1992 | Kiri et al. ................ 250/208.1 |
| 5,237,598 A | | 8/1993 | Albert |
| 5,357,110 A | * | 10/1994 | Statham ...................... 250/307 |
| 5,379,334 A | * | 1/1995 | Zimmer et al. ............ 378/98.2 |
| 5,464,013 A | * | 11/1995 | Lemelson ................ 128/653.1 |
| 5,493,517 A | * | 2/1996 | Frazier ........................ 702/33 |
| 5,493,596 A | | 2/1996 | Annis |
| 5,541,856 A | | 7/1996 | Hammermeister |
| 5,638,420 A | | 6/1997 | Armistead |
| 5,692,028 A | | 11/1997 | Geus et al. |
| 5,754,617 A | | 5/1998 | Itoh |
| 5,764,683 A | | 6/1998 | Swift et al. |
| 5,903,623 A | | 5/1999 | Swift et al. |
| 5,910,973 A | | 6/1999 | Grodzins |
| 5,936,249 A | | 8/1999 | Eisen et al. |
| 6,031,890 A | | 2/2000 | Bermbach et al. |
| 6,058,158 A | | 5/2000 | Eiler |
| 6,255,654 B1 | * | 7/2001 | Verbinski et al. ......... 250/358.1 |
| 6,415,048 B1 | * | 7/2002 | Schneider .................... 378/20 |

OTHER PUBLICATIONS

U.S. application Ser. No. 08/546,999, titled "Density Detection using Discrete Photon Counting," filed Oct. 23, 1995 (now abandoned), relied on under 35 U.S.C. §120.

"SAIC's Vacis II to Search for Contraband at U.S. Borders—U.S. Customs Services Issues Contracts for 29 VACIS IIs" [online], Jul. 30, 1999 [retrieved on Apr. 30, 2002], 1 p., Retrieved from the Internet: http://www.laprensa-sandiego.org/archieve/july30/vacis.htm.

"Vehicle & Cargo Inspection System" [online], Xtek General Security Products, Copyright 2001 [retrieved on Apr. 30, 2002], 1 p., Retrieved from the Internet: http://www.xtek.net/catalogue/general/vacis.shtml.

Emery, Gail Repsher, "SAIC Sells Imaging Systems to Customs Service" [online], Mar. 20, 2001 [retrieved on Apr. 30, 2002], 2 pp., Retrieved from the Internet: http://www-.washingtontechnology.com/news/1_1/daily_news/16302-1.html.

"U.S. Customs Service Orders Nine Railroad VACIS Units—SAIC's VACIS Technology to Be Used for Rail Car Inspections at Major U.S. Rail Border Locations" [online], May 21, 2001 [retrieved on Apr. 30, 2002], 2 pp., Retrieved from the Internet: http://www.saic.com/news/may01/news05-21-01.html.

McBee, Christopher J., Bowlin, David W. and Orphan, Victor J., "Mobile Cargo Inspection Provides Improved Throughput Efficiency and Flexibility," *Port Technology International*, 4 pp.

Snell, Michael P., "Gamma–Ray Technology: The Practical Container Inspection Alternative," *Port Technology International*, 6 pp.

Richardson, Rex D., Verbinski, Victor V. and Orphan, Victor J., "New VACIS Applications and Performance Enhancements," 16 pp.

"VACIS—SAIC's Vehicle and Cargo Inspection Systems," 10 pp.

"U.S. Customs Service Inspectors Seize 2,362 Pounds of Marijuana at El Paso Port of Entry" [online], Mar. 8, 2002 [retrieved on May 22, 2002], 1 p., Retrieved from Internet: http://www.customs.gov/hot–new/pressrel/2002/0311–00.htm.

"U.S. Customs Service Inspectors Seize 234 Pounds of Cocaine at Presidio Port—High Tech Tools Help Pinpoint Drug Load" [online], Feb. 13, 2002 [retrieved on May 22, 2002], 1 p., Retrieved from Internet: http://www.customs.gov/hot–new/pressrel/2002/0215–03.htm.

"U.S. Customs Service Inspectors Make Record Seizure at Santa Teresa Port—More Than 2½ Tons of Marijuana Confiscated" [online], Feb. 4, 2002 [retrieved on May 22, 2002], 1 p., Retrieved from the Internet: http://www.customs.gov/hot–new/pressrel/2002/0207–01.htm.

"U.S. Customs Service Inspectors Locate 1,700 Pound Marijuana Load—Seizure is One of Five Made at Nogales Tuesday" [online], Jan. 30, 2002 [retrieved on May 22, 2002], 1 p., Retrieved from the Internet: http://www.customs.gov/hot–new/pressrel/2002–0207–00.htm.

"U.S. Customs Inspectors in South Texas Seize $5.3 Million in Narcotics Over Veteran's Day Weekend" [online], Nov. 13, 2001 [retrieved on May 22, 2002], 1 p., Retrieved from the Internet: http://www.customs.gov/hot–new/pressrel/2001/1115–01.htm.

"U.S. Customs Inspectors Seize Over a Ton of Marijuana in Bus at Lincoln–Juarez Bridge, Two Arrested" [online], Nov. 6, 2001 [retrieved on May 22, 2002], 1 p., Retrieved from the Internet: http://www.customs.gov/hot–new/pressrel/2001/1106–00.htm.

"U.S. Customs Inspectors Seize 181 Pounds of Cocaine at Hidalgo/Pharr Port of Entry in Past Few Days" [online], Oct. 3, 2001 [retrieved on May 22, 2002], 2 pp., Retrieved from the Internet: http://www.customs.gov/hot–new/pressrel/2001/1004–01.htm.

"U.S. Customs Seizes Significant Marijuana Load in Bus at Roma Port of Entry" [online], Aug. 8, 2001 [retrieved on May 22, 2002], 1 p., Retrieved from the Internet: http://www.customs.gov/hot–new/pressrel/2001/0808–02.htm.

"Customs Inspectors in Naco and Nogales Stop Commercial Trucks Loaded With Dope—Seizures Net More Than 2,300 Pounds of Marijuana" [online], Jul. 20, 2001 [retrieved on May 22, 2002], 1 p., Retrieved from the Internet: http://www.customs.gov/hot–new/pressrel/2001/0720–02/htm.

"U.S. Customs Service Makes Record Drug Seizure At Santa Teresa Port of Entry" [online], Jul. 13, 2001 [retrieved on May 22, 2002], 1 p., Retrieved from the Internet: http://www.customs.gov/hot–new/pressrel/2001/0718–01.htm.

"U.S. Customs Seizes $18 Million Load of Marijuana–Encased Cocaine From Commercial Bus in Eagle Pass" [online], Jul. 2, 2001 [retrieved on May 22, 2002], 1 p., Retrieved from the Internet: http://www.customs.gov/hot–new/pressrel/2001/0702–01.htm.

"Customs Seizes Marijuana from Two Commercial Trucks" [online], May 21, 2001 [retrieved on May 22, 2002], 1 p., Retrieved from the Internet: http://www.customs.gov/hot–new/pressrel/2001/0523–02.htm.

"U.S. Customs Inspectors Locate 1,296 Pound Marijuana Load in Commercial Truck at Nogales Port" [online], May 18, 2001 [retrieved on May 22, 2002], 1 p., Retrieved from the Internet: http://www.customs.gov/hot–new/pressrel/2001/0518–04.htm.

"U.S. Customs Seizes Ton of Marijuana in Back–To–Back Seizures at World Trade Bridge Last Night—Inspectors Have Seized 4,407 Pounds at World Trade Bridge in Past Week" [online], May 11, 2001 [retrieved on May 22, 2002], 1 p., Retrieved from the Internet: http://www.customs.gov/hot–new/pressrel/2001/0514–01.htm.

"U.S. Customs Inspectors Seize More Than Half–A–Million in Cash in Roma, One Arrested" [online], May 9, 2001 [retrieved on May 22, 2002], 1 p., Retrieved from the Internet: http://www.customs.gov/hot–new/pressrel/2001/0509–01.htm.

"U.S. Customs Inspectors Seize 3,089 Pounds of Marijuana at World Trade Bridge" [online], May 1, 2001 [retrieved on May 22, 2002], 1 p., Retrieved from the Internet: http://www.customs.gov/hot–new/pressrel/2001/0502–02.htm.

"U.S. Customs Seizes Over a Ton in Off–Road Trailer" [online], Mar. 13, 2001 [retrieved on May 22, 2002], 1 p., Retrieved from the Internet: http://www.customs.gov/hot–new/pressrel/2001/0315–00.htm.

"U.S. Customs Seizes More Than 3,300 Pounds of Marijuana Hidden Inside Cargo Container" [online], Mar. 9, 2001 [retrieved on May 22, 2002], 1 p., Retrieved from the Internet: http://www.customs.gov/hot–new/pressrel/2001/0313–00.htm.

"U.S. Customs Inspectors Seize $1.5 Million in Cocaine, Currency, Methamphetamine and Marijuana This Weekend at Port of Entry" [online], Feb. 12, 2001 [retrieved on May 22, 2002], 1 p., Retrieved from the Internet: http://www.customs.gov/hot–new/pressrel/2001/0213–02.htm.

"U.S. Customs Service Inspectors Seize 4,946 Pounds of Marijuana at El Paso/Ysleta Cargo Facility" [online], Jan. 30, 2001 [retrieved on May 22, 2002], 1 p., Retrieved from the Internet: http://www.customs.gov/hot–new/pressrel/2001/0130–02.htm.

"U.S. Customs Inspectors Seize 2,939 Pounds of Marijuana at World Trade Bridge This Weekend" [online], Jan. 29, 2001 [retrieved on May 22, 2002], 1 p., Retrieved from the Internet: http://www.customs.gov/hot–new/pressrel/2001/0130–01.htm.

* cited by examiner

DENSITY DETECTION USING DISCRETE PHOTON COUNTING

This is a Continuation of application Ser. No. 09/398,980, for DENSITY DETECTION USING PHOTON COUNTING, filed Sep. 17, 1999, by Verbinski, et al., now U.S. Pat. No. 6,255,654 issued Jul. 3, 2001, which is a Continuation of application Ser. No. 08/921,854, for DENSITY DETECTION USING DISCRETE PHOTON COUNTING, filed Sep. 2, 1997, by Verbinski, et al., now abandoned, which is a Continuation of application Ser. No. 08/546,999, for DENSITY DETECTION USING DISCRETE PHOTON COUNTING, filed Oct. 23, 1995, by Verbinski, et al., now abandoned, all of which are incorporated herein by reference.

A portion of the disclosure of this patent document contains material that is subject to copyright protection. The copyright owner has no objection to the facsimile reproduction by anyone of this patent document or the patent disclosure, as it appears in the United States Patent and Trademark Office patent files or records, but otherwise reserves all copyright rights whatsoever.

BACKGROUND OF THE INVENTION

COMPUTER PROGRAM LISTING APPENDIX

A computer program listing appendix is submitted herewith on a single compact disc. The computer program listing is incorporated-by-reference herein in its entirety. The compact disc is a CD-R disc labeled "09/834,377apx" and contains a single computer program listing that was saved to CD-R on Aug. 6, 2002 and is 3.5 MB.

The present invention relates to density detection using discrete photon counting, and more particularly to using discrete photon counting to generate an image indicative of the densities in a target object. Even more particularly, the present invention relates to using discrete photon counting to perform density measurements in a target object and generating an image of the contents of such target object in response thereto.

There are many instances in the security or customs field when it is necessary to examine or inspect, in a non-destructive way, the contents of a target object, such as a closed package, box, suitcase, cargo container, automobile semi-trailer, tanker truck, railroad car, e.g., box car or tanker car, or the like. For example, customs departments are routinely charged with the responsibility of inspecting vehicles coming into a country to make sure such packages do not contain drugs or other contraband. Similarly, drug smugglers frequently carry out their criminal acts by hiding illegal drugs in vehicles such tanker trucks, and then sending the trucks through a border checkpoint. When security personnel encounter suspicious vehicles or other containers being transported over international boundaries, they must perform a careful inspection of such vehicles to ascertain their contents.

When suspicious vehicles are discovered, they generally must be examined or inspected on location in what is referred to as a "secondary inspection area." If secondary inspection reveals the presence of contraband (e.g., drugs), then the vehicle may be impounded, the driver arrested, and the contraband disposed of. If, on the other hand, the examination reveals the absence of contraband, then the vehicle may be allowed to proceed in a normal manner.

The process used to examine or inspect a suspicious vehicle should be quick, simple, and as unintrusive as possible. Unfortunately, conventional inspection mechanisms require either visual inspection by others and/or scent inspection by dogs. These conventional methods require that the vehicle stop and wait for the inspection to be completed, which can take a half hour or more. This is both inconvenient and time consuming for both customs officials and the vehicle drivers and occupants. Furthermore, such inspection may put officers at personal risk if a vehicle has been booby trapped or if the vehicle's driver or other occupants become nervous and decide to attack the customs officer inspecting their vehicle. What is needed, therefore, is a non-invasive technique for inspecting the contents of a suspicious vehicle without requiring that the vehicle be stopped and manually inspected.

One attempt to satisfy this need involves the use of high levels of radiation to determine the densities of the vehicle and/or the contents of such vehicle. Unfortunately, this approach requires that the vehicle be stopped and evacuated prior to inspection, because such high levels of radiation can be physically harmful to the vehicle's occupants if they remain in the vehicle during inspection. Disadvantageously, inspection using high levels of radiation not only requires that the vehicle be stopped, and therefore delayed, but poses a risk to stowaways that may be aboard the vehicle, and unwilling to voluntarily evacuate, when the vehicle is stopped for inspection. Therefore, what is needed is a non-invasive technique for inspecting the contents of a suspicious vehicle without requiring the use of high levels of radiation.

A further problem posed by manual inspection techniques arises when tanker trucks or railroad cars, after having been emptied, seek to cross a border in order to refill. Because such tankers cannot be completely emptied without releasing the pressure in such tankers and venting noxious gases into the atmosphere, the tankers typically are kept nominally under pressure. The venting of noxious gases would be hazardous and ecologically unacceptable. The contents of such tankers typically go uninspected by customs agents in order to avoid the venting of such gases. Unfortunately, drugs smugglers are well aware of this fact, and therefore utilize tanker trucks and railroad cars to import illegal drugs, knowing that they will not be inspected at the border. This provides just one of numerous additional examples of cases where invasive or intrusive inspection into vehicles, or other containers, is not feasible or desirable. Thus, further emphasizing the need for a non-intrusive approach to vehicle inspection.

The present invention advantageously addresses the above and other needs.

SUMMARY OF THE INVENTION

The present invention advantageously addresses the needs above as well as other needs by providing a system and method employing discrete photon counting to perform density measurements in a target object and generate to an image of the contents of such target object in response thereto.

In one embodiment, the present invention can be characterized as a system for detecting densities within an target object. The system employs a radiation source; a detector array comprising a plurality of radiation detectors; an electrical subsystem coupled to the detector array; and a display device for displaying a graphical representation of the densities within the target object in response to a display output signal. The electrical subsystem discretely counts the number of photons detected by each radiation detector; and generates the display output signal in response thereto.

In another embodiment, the present invention can be characterized as a method of detecting densities within a target object. The method has the steps of irradiating the target object; detecting a first discrete number of photons penetrating the target object through a first prescribed volume and entering a first radiation detector; and detecting a second discrete number of photons penetrating the target object through a second prescribed volume and entering a second radiation detector. Next, the method involves discretely counting a first number of photons detected by the first radiation detector; discretely counting a second number of photons detected by the second radiation detector; and generating a display output signal in response to the first number of photons and the second number of photons. The display output signal is used to display a graphical representation of the densities within the first volume of the target object and the second volume of the target object.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE PREFERRED EMBODIMENTS

The following description of the presently contemplated best mode of practicing the invention is not to be taken in a limiting sense, but is made merely for the purpose of describing the general principles of the invention. The scope of the invention should be determined with reference to the claims.

Figure 1:
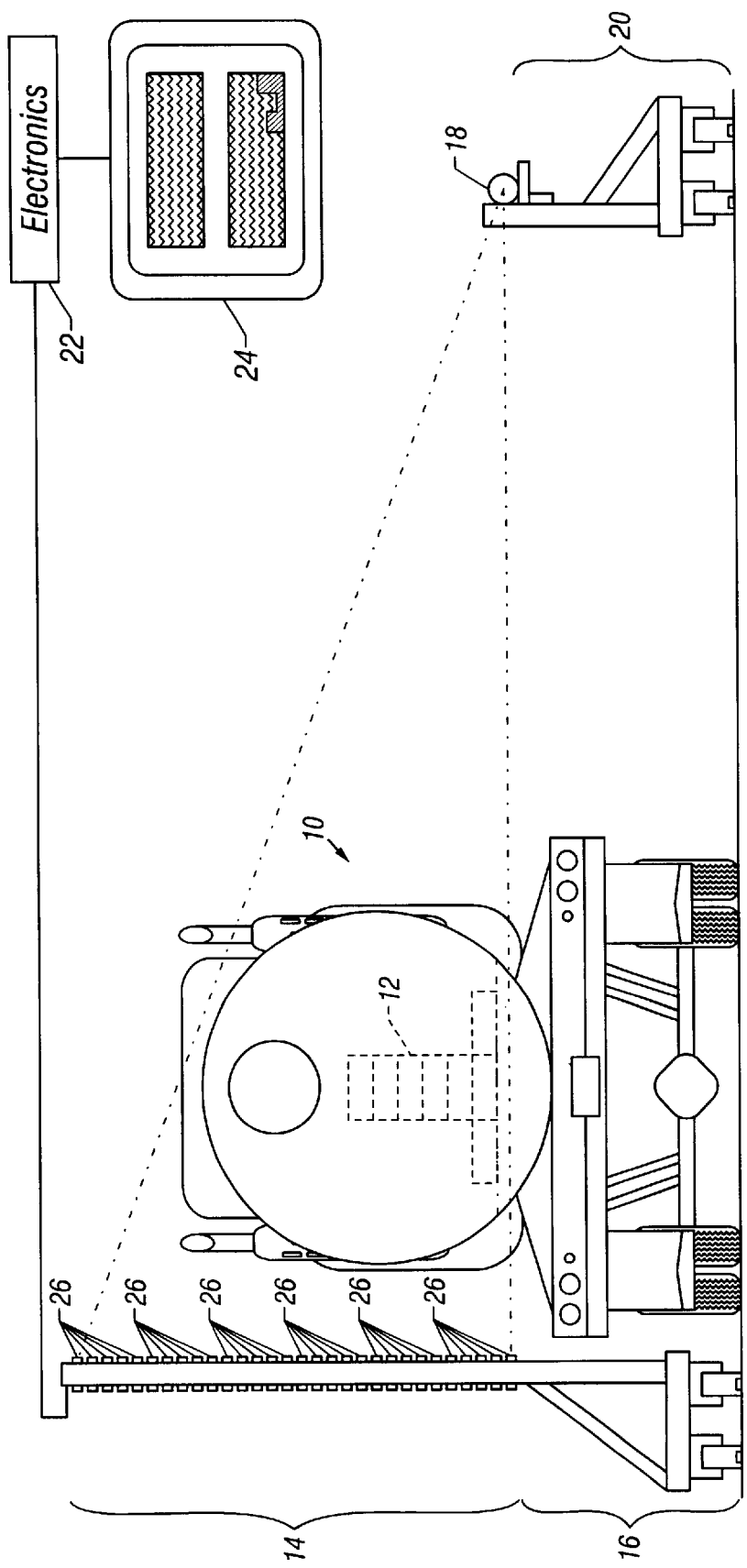
FIG. 1 is a schematic diagram of a system made in accordance with one embodiment of the present invention and of a tanker truck containing contraband material, wherein discrete photon counting is used to perform density measurements in a tanker truck and wherein an image is generated of the contents of such tanker truck in response thereto.

Referring first to FIG. 1, a schematic diagram is shown of a system made in accordance with one embodiment of the present invention and of a tanker truck containing contraband material, wherein discrete photon counting is used to perform density measurements in the tanker truck and wherein an image is generated of the contents of such tanker truck in response thereto.

Shown are the tanker truck 10, concealed contraband 12, a detector array 14, a detector array truck 16, a radiation source 18, a radiation source truck 20, processing electronics 22 and a graphical display device 24.

The detector array 14 employs a plurality of "oversized" high efficiency gamma-ray detectors 26, e.g., between twenty and sixty, e.g., forty-eight, detectors arranged in a vertical column. The detectors 26 make it possible to scan the tanker truck 10 with a very low intensity gamma-ray field. In order to facilitate the use of very low intensity gamma-radiation, oversized detectors 26 are used, such as are available as Part No. 1.5M1.5M1.5, NaI (Tl) (sodium iodide crystal, thallium activated) (with R2060 photomultiplier tube) from BICRON of Ohio. Such gamma-ray detectors are scintillation counter-type detectors and are 3.8 cm in diameter, 3.8 cm high and mounted on a 3.8 cm photomultiplier tube (PMT).

The very low intensity gamma-ray field useable with gamma-ray detectors 26 is low enough in intensity to allow operating personnel to work within it. For example, the very low intensity gamma-ray field may use 662 keV gamma-ray energy. However, a stronger gamma-ray or x-ray source than this can be used in the interest of faster density measurements, while still allowing operating personnel to work within the very low intensity field. Such can be used for example when the vehicle under inspection is travelling at high speeds.

The radiation source 18 is preferably a $3.7 \times 10^{10}$ Bq shuttered source of Cs-137 gamma-rays, i.e., 662 keV gamma-ray energy. Alternatively, a Co-60 source may be used. A suitable source is readily available as Model No. SH-F-2 from Ohmart Corporation of Ohio. The radiation source includes a collimator that provides a 45° vertical opening, measured from horizontal upwards, and a 10° lateral opening. The shutter is electrically actuated.

The radiation source 18 provides gamma-rays that are only moderately attenuated by steel walls typically found in tanker trucks or railroad cars. Yet such rays are sufficiently attenuated by contraband packages to make them easily detectable by measuring the penetration of the gamma-rays emitted from the source and deriving relative material densities therefrom. In addition, there is negligible backscattering of the gamma-ray energy from the tanker walls, much less than would occur if a high-powered x-ray source was utilized, although an x-ray source may be desirable for high speed inspection applications or for inspection of unmanned vehicles.

The detector array truck 16 and the radiation source truck 20 are designed to travel synchronously along parallel tracks. The trucks 16, 20, the tracks, a synchronous drive motor and a variable frequency generator for controlling the speed of the synchronous drive motors are available as Model No. SA0100 from Becker Equipment (Maakh Becker P.E.) of Vista, Calif., however, numerous known substitutes can be employed.

In operation, the trucks 16, 20 are moved synchronously along parallel paths spanning the entire length of the tanker truck or the railroad car to be inspected by the synchronous drive motors. Alternatively, and preferably, the truck or railroad car being inspected can be driven between the detector array 14 and the radiation source 18, which in such alternative are both stationarily mounted.

The vertical "linear array" configuration of the detectors 26 is made to provide a resolution of grid points spaced about every 5 cm along the length of the target vehicle, and about 4.3 cm, on average, along the height of the target vehicle, as projected on the target vehicle vertical center plane, running lengthwise. This resolution is adequate to achieve a detectability limit of less than half a kilogram of contraband per 4.3 cm by 5 cm gridpoint, or pixel. The pixel size can easily be varied by appropriately selecting the location of the radiation source and the detectors 26 within the detector array 14, and by varying the distance between inspection points longitudinally via choice of counting interval and scan speed along the length of the target vehicle.

Preferably, the entire length of the tanker truck or railroad car is scanned automatically, in a single sweep. In order to accomplish automatic scanning in the truck-mounted embodiment shown, the detector array truck 16 and the radiation source truck 20 are moved in a parallel fashion along the tracks at a constant speed, with a counting interval selected to effect a longitudinal pixel length (i.e., grid-spacing interval) of 1 to 2 inches for a typical tanker truck inspection. This grid size, as mentioned above, can easily be selected by one skilled in the art based on the disclosure provided herein and dependent upon an optimum tradeoff between minimum contraband content detectability, throughput (i.e., inspection time per tanker truck), gamma-ray field-strength (and other safety considerations), and overall system cost.

As mentioned above, if a sufficiently high field-strength is utilized, the detector array 14 and the radiation source 18 may be fixed or stationary rather than mounted on the radiation source truck 20 and the detector array truck 16. In such an arrangement, the tanker truck 10 or railroad car can be driven past the detector array 14 and radiation source 18 with the determination as to the densities within the tanker truck 10 being made automatically as the tanker truck 10 passes between the radiation source 14 and the detector array 18.

Thus, in the embodiment shown in FIG. 1 and in the preferred embodiment, a truly non-invasive inspection technique is provided in which there is no need to evacuate the vehicle to be inspected, or, in the preferred embodiment, to even stop or slow down the vehicle in order to effect inspection of such vehicle.

Figure 2:
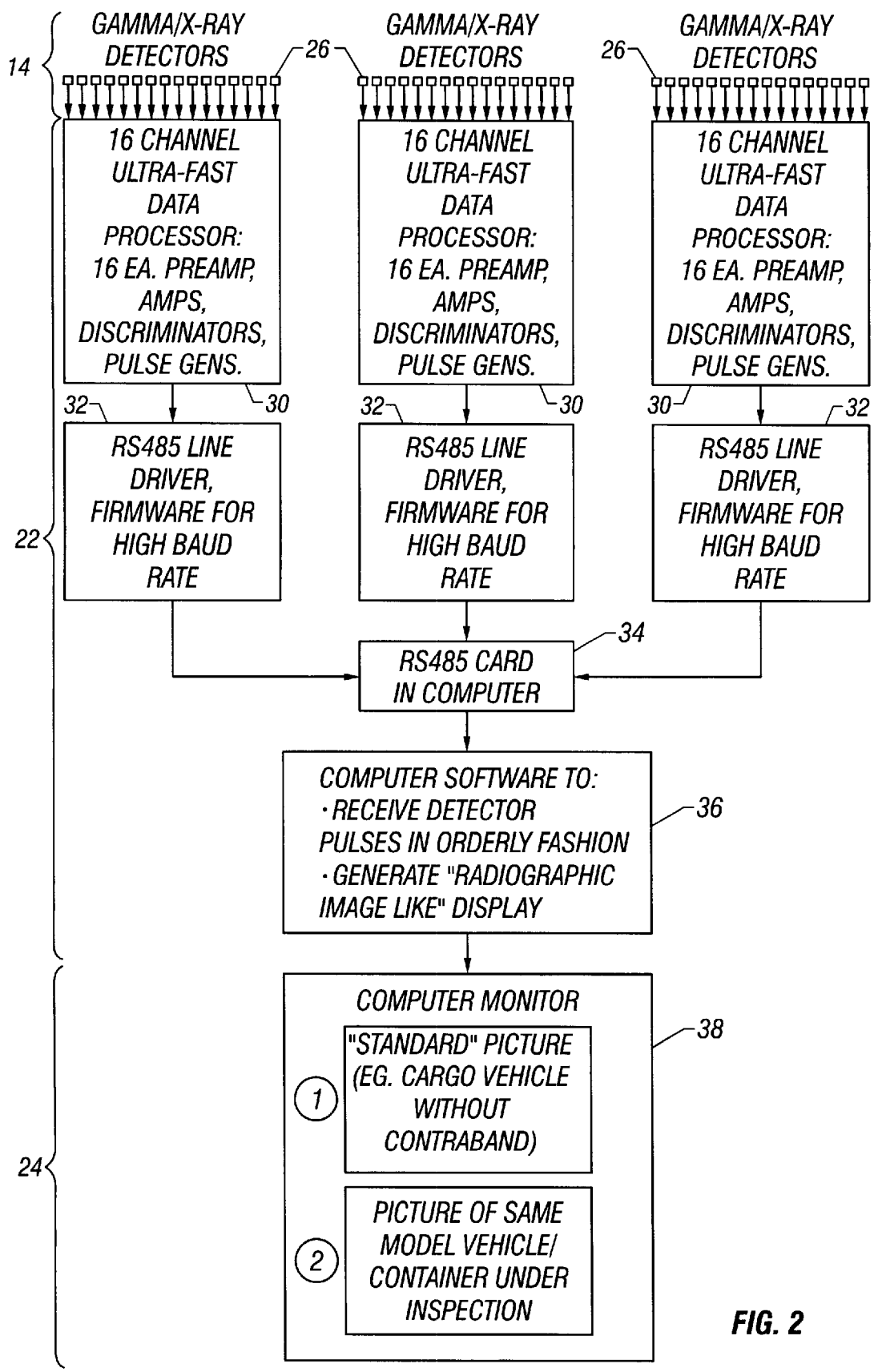
FIG. 2 is a block diagram of the system of FIG. 1 showing gamma/x-ray detectors coupled through 16-channel processing units, RS-485 line drivers, and an RS-485 interface card to a computer, wherein the computer processes discrete photon count information received from the detectors and causes a display device to display an image of the contents of a target object, such as the tanker truck of FIG. 1, in response thereto.

Referring next to FIG. 2, a block diagram is shown of the system of FIG. 1 showing gamma/x-ray detectors coupled through 16-channel processing units, RS-485 line drivers, and an RS-485 interface card to a computer, wherein the computer processes discrete photon count information received from the detectors and causes a display device to display an image of the contents of a target object, such as the tanker truck of FIG. 1, in response thereto.

The detector array 14 is depicted, as are the electronics 22 and the graphical display device 24. The detector array 14 employs the plurality of gamma/x-ray detectors 26. The gamma/x-ray detectors 26 are coupled in groups of 16 to 16-channel data processing circuits 30. Preferably, three groups of gamma/x-ray detectors 26 are used. In practice, the number of gamma/x-ray detectors 26 used depends on the height of the vehicles to be inspected and the resolution, i.e., number of pixels, in the image desired. In a preferred embodiment, 48 gamma/x-ray detectors are used.

The data processing circuits 30, of which there are preferably three, are each coupled to an RS-485 line driver 32, which is coupled to an RS-485 interface 34. The RS-485 interface 34 is embodied on a circuit card located within a computer system 36. A suitable RS-485 interface is available as Model No. 516-485, Part No. 3054 from Seal Level Systems, Inc., and from numerous other vendors under respective model/part number designations.

The computer system 36, which is preferably a Pentium-90 based personal computer system, operates programmatically under the control of a software system. The computer system 36 receives detector pulses from each of the 16-channel data processors 30, in response to the detection of individual photons by the gamma/x-ray detectors 26. As explained in further detail hereinbelow, the software system processes the incoming detector pulses, evaluating their relative amplitudes, i.e., energies, and generates a radio graphic image-like display output signal in response thereto. The radio graphic, image-like display output signal is coupled to the graphical display device 38, which is preferably a Super-VGA monitor, and is used by the graphical display device 38 to generate a graphical representation of the densities within the vehicle under inspection.

Unlike prior art systems, which do not generate a graphical representation, i.e., a "picture", of the densities of the contents of the vehicle under inspection, the present embodiment generates such a picture. Advantageously, this allows for easy visual interpretation of the results of the scanning of the vehicle under inspection, as opposed to interpreting more subtle indications of the densities within the vehicle under inspection as may be required in prior art systems.

Advantageously, the preferred software system also causes the display of a reference image simultaneous with the image generated in response to the vehicle under inspection, so that an operator of the present embodiment can easily make a visual comparison between what a vehicle of the type being inspected should "look like", and what the vehicle under inspection actually "looks like". Such "side-by-side" inspection further simplifies the detection of contraband using the present embodiment.

As a result of the very low intensity gamma-ray or X-ray radiation used by the present embodiment, photon penetration, as opposed to backscatter, can be used to generate a side, as opposed to a bottom/top, image of the vehicle under inspection. This represents a significant improvement over prior art systems wherein a bottom/top presentation of the radiation source is required to avoid the need for excessive radiation shielding, but dictates that the vehicle's frame, drive train, etc., interface with the density measurements taken based on radiation penetration. Backscatter-type density measurement systems are less accurate due to the non-uniform backscattered radiation on which they rely for density measurement.

Figure 3:
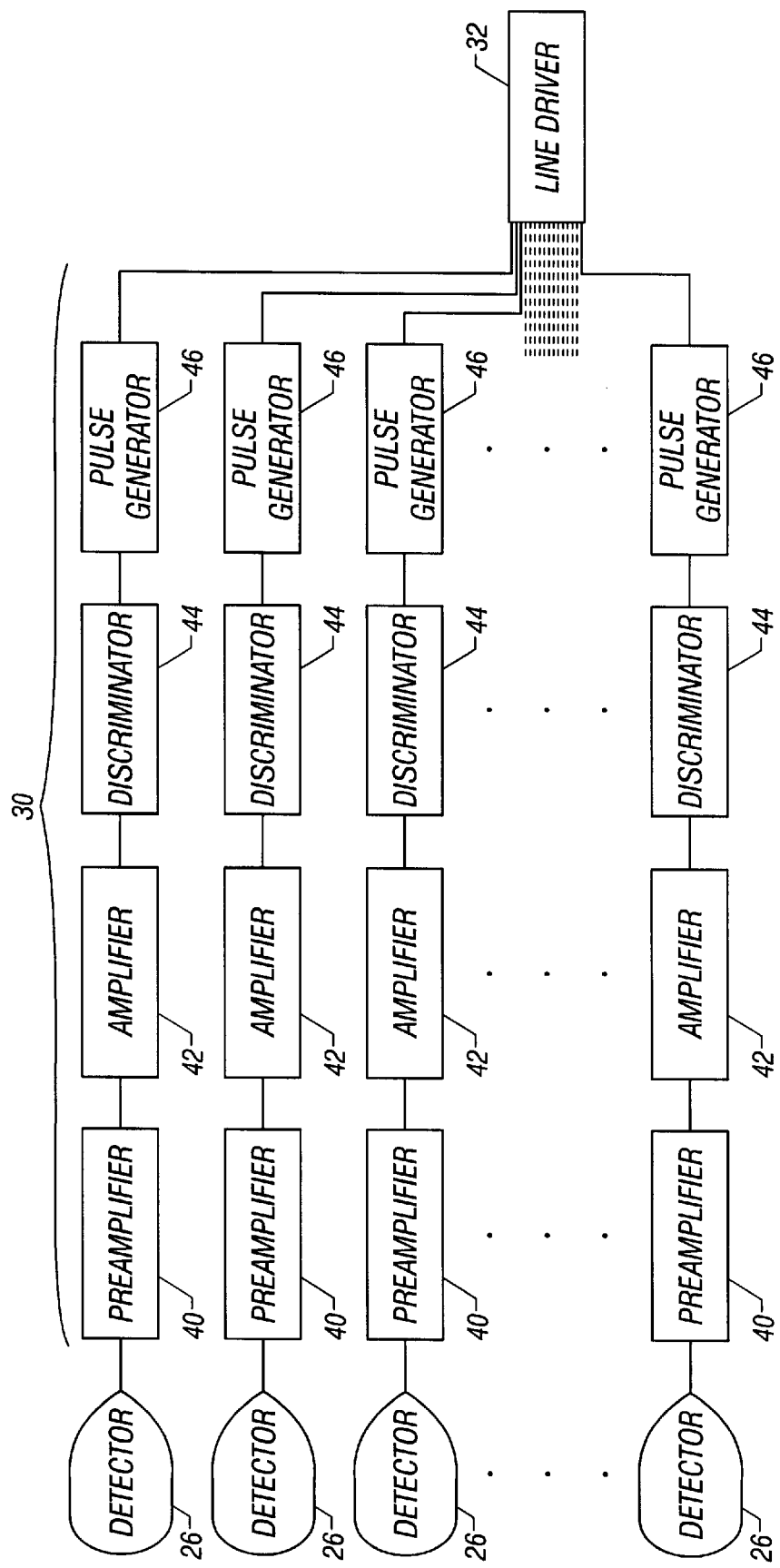
FIG. 3 is a block diagram showing the detectors of FIG. 2 coupled through preamplifiers, amplifiers, discriminators, pulse generators and an RS-485 line driver that make up one embodiment of the 16-channel processing units of FIG. 2.

Referring next to FIG. 3, a block diagram is shown of the detectors of FIG. 2 coupled through preamplifiers, amplifiers, discriminators, pulse generators and an RS-485 line driver that make up one embodiment of the 16-channel processing units of FIG. 2.

Each of the radiation detectors 26 is coupled to preamplifier 14 within the 16-channel data processing nit 30. Each preamplifier 14 is coupled to an amplifier 42, which is in turn coupled to a discriminator 44. Each discriminator 44 is coupled to a pulse generator 46, which generates an electrical pulse for each photon received into the radiation detector 26 coupled thereto. Because very low intensity gamma-ray or x-ray radiation is used with the present embodiment, pulse pileup is generally not of significant concern.

The pulse generators 46 within each of the 16-channel data processing units 30 are coupled to a line driver 32. Each of the 16-channel data processing units 30 includes its own line driver 32. The line drivers 32 operate under the programmatic control of a firmware operating system, such as shown in APPENDIX A.

In operation, the preamplifiers 40, and amplifiers 42 function in a conventional manner to amplify signals generated by the detectors 26. Outputs of the amplifiers 42 are passed along to the discriminators 44, which impose a noise threshold on the amplified signal. Waveforms within the amplified signal that exceed the noise threshold are passed along to the pulse generator, which generates a pulse for each waveform within the amplified signal corresponding to a received gamma-ray or x-ray photon.

The line driver 32 passes the pulses generated by each of the pulse generators 46 within a particular 16-channel data processing unit 30 along to the computer via the RS-485 interface 34.

Referring next to FIGS. 4A, 4B, 4C, 4D, 4E, 4F, 4G, 4H and 4I, a schematic diagram is shown of one variation of an analog portion the 16-channel processing units of FIGS. 2 and 3. The schematics of FIGS. 4A, 4B, 4C, 4D, 4E, 4F, 4G, 4H and 4I are self-explanatory to one of skill in the art and therefore further explanation of these figures is not made herein.

Figures 1, 5A:
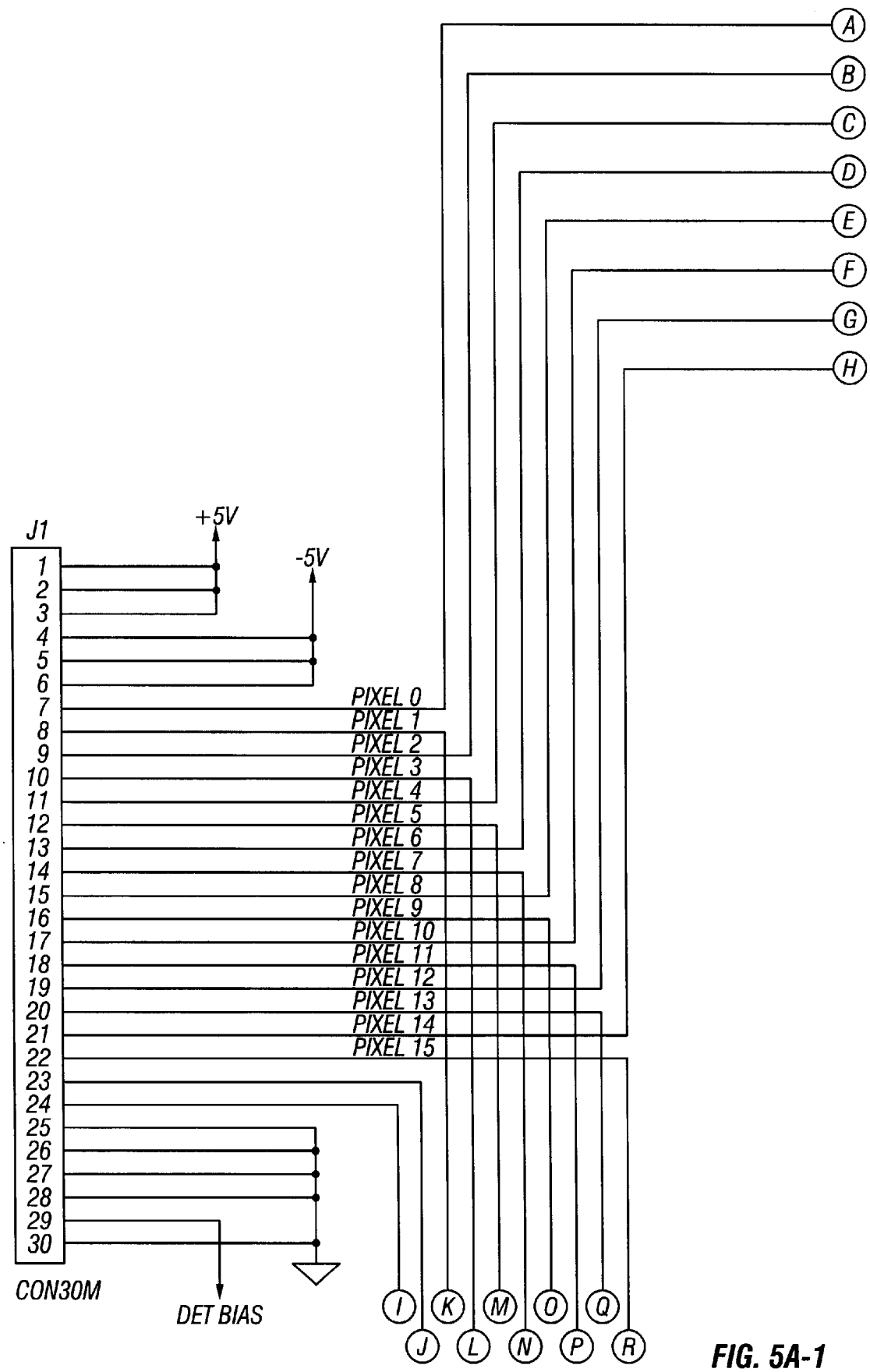
FIGS. 5A, 5B and 5C are a schematic diagram showing one variation of a digital portion of the 16-channel processing units of FIGS. 2 and 3.
Figures 2, 5A:
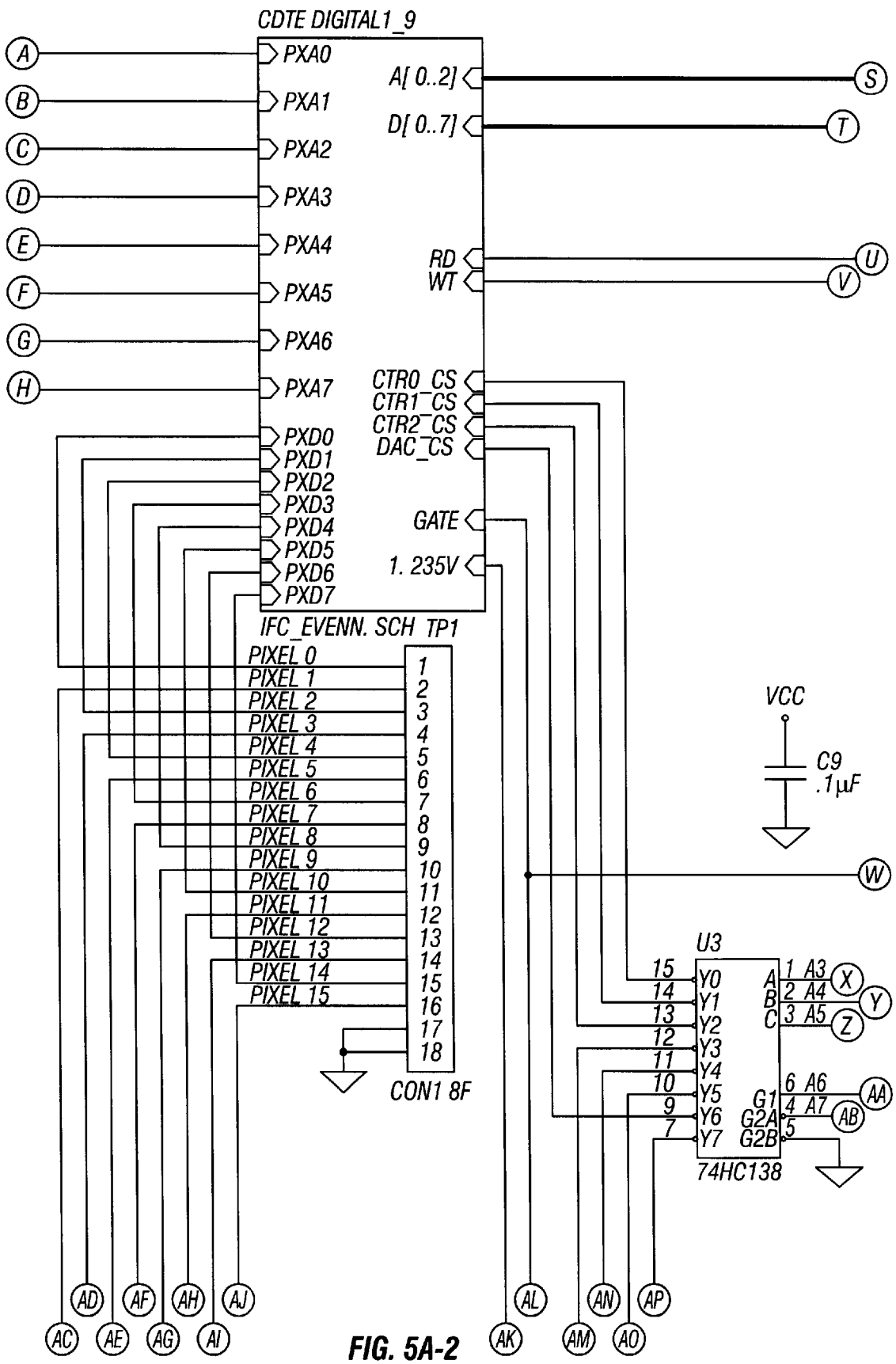
Figures 3, 5A:
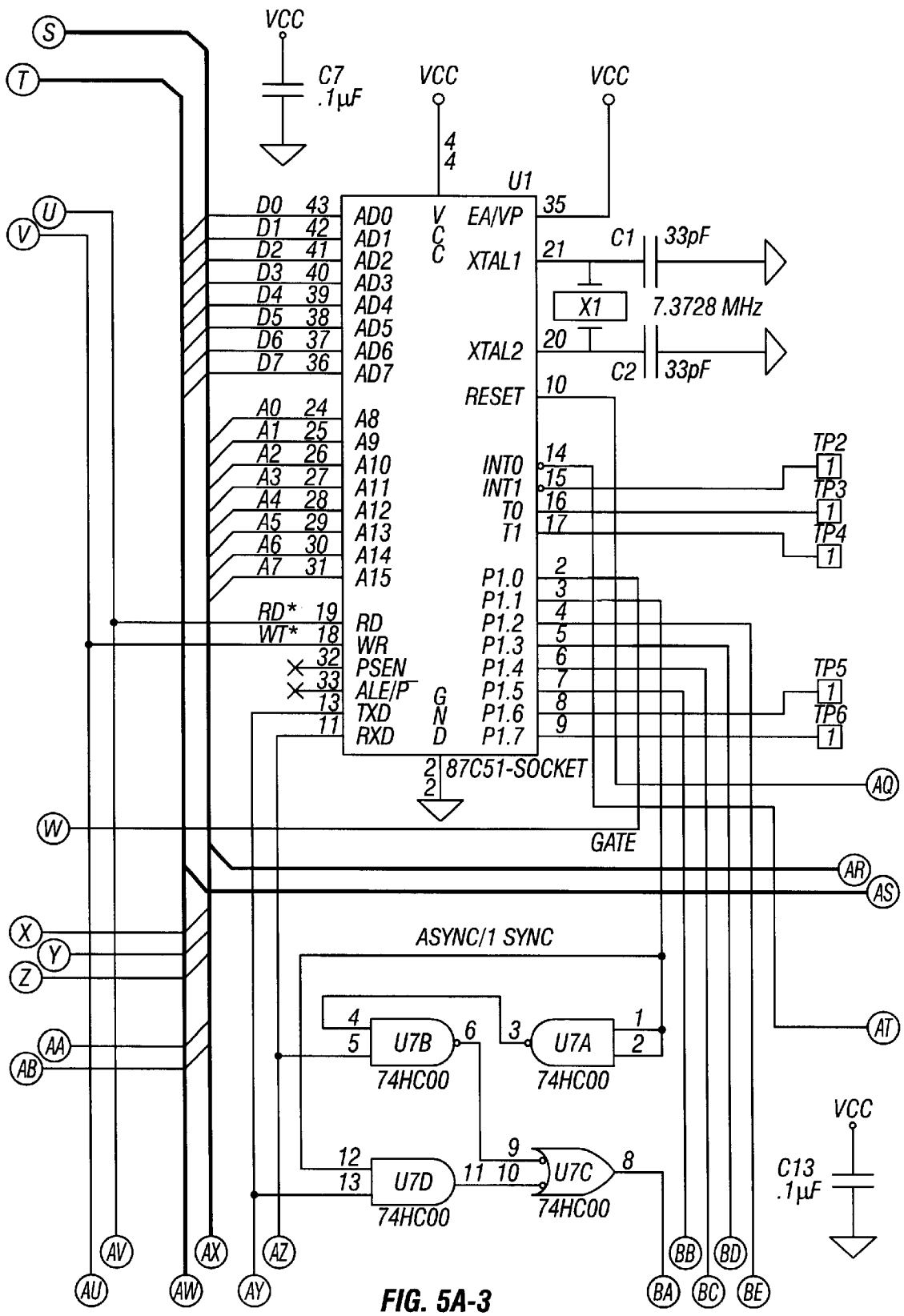
Figures 4, 5A:
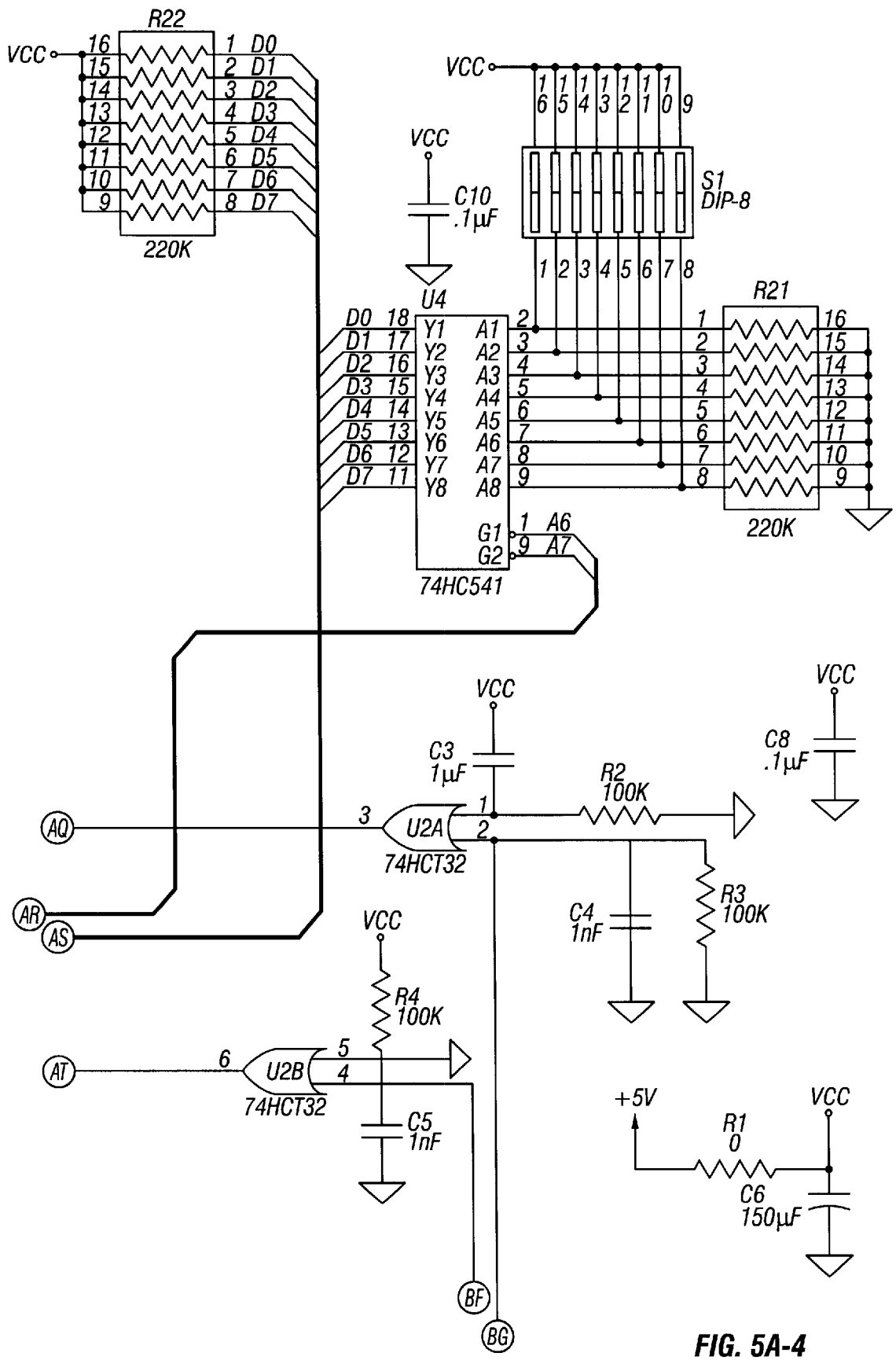
Figures 5, 5A:
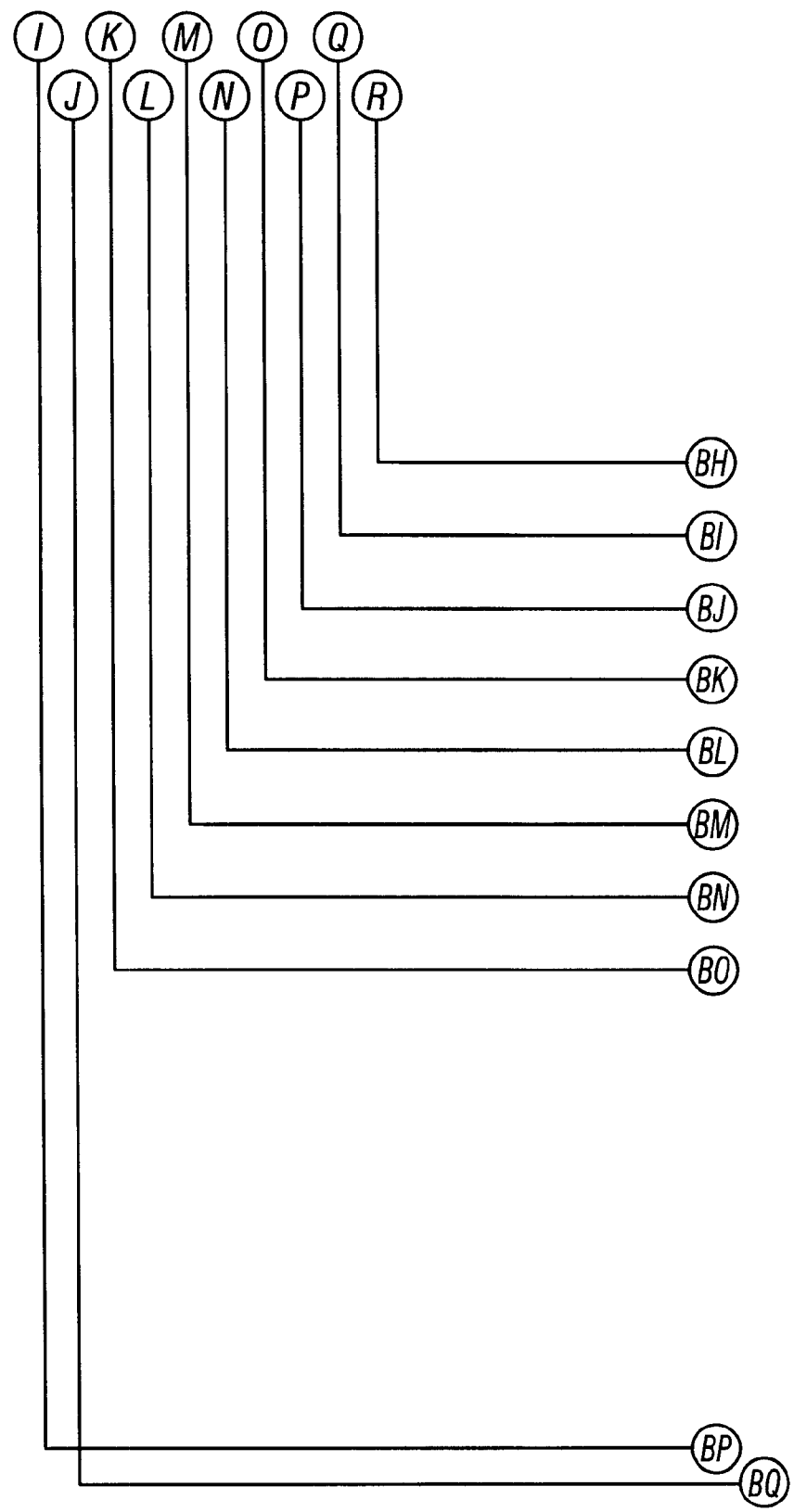
Figures 5, 5A, 6:
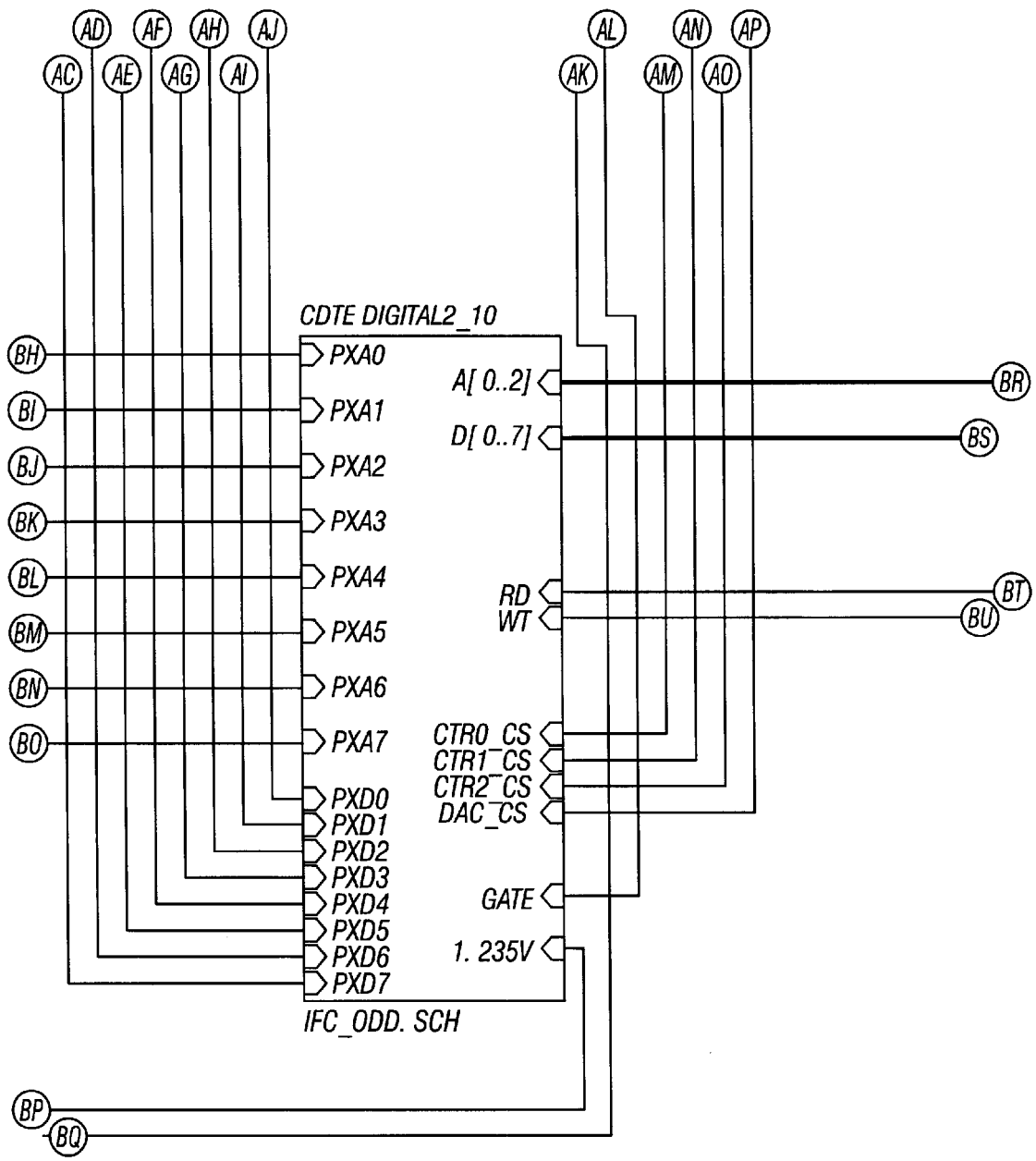
Figures 5, 5A, 6, 7:
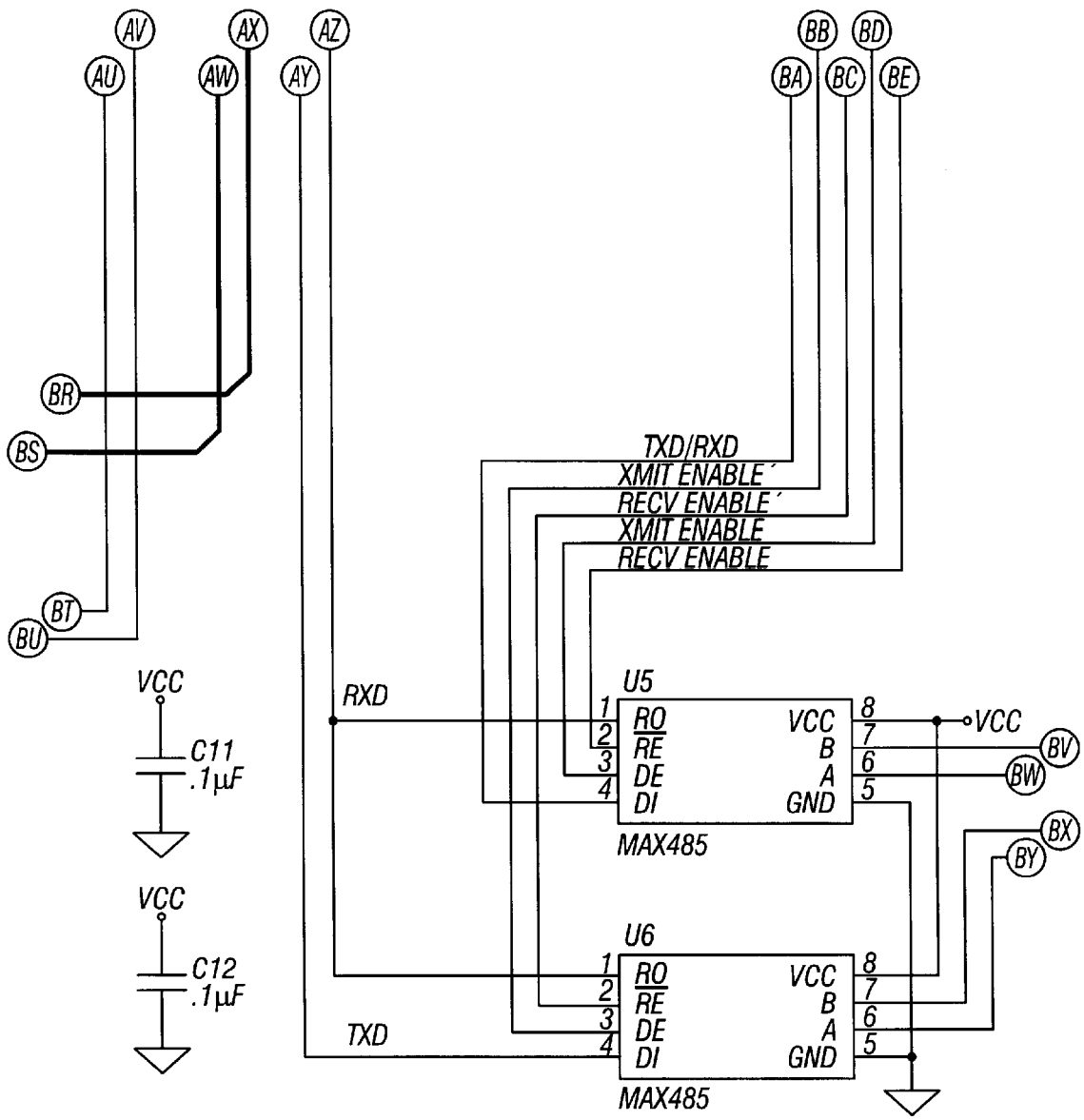
FIG. 7 is a flow chart showing the steps traversed by the computer of FIG. 2 in response to the software system of FIG. 6 when an image generation program is executed.
Figures 5, 5A, 6, 7, 8:
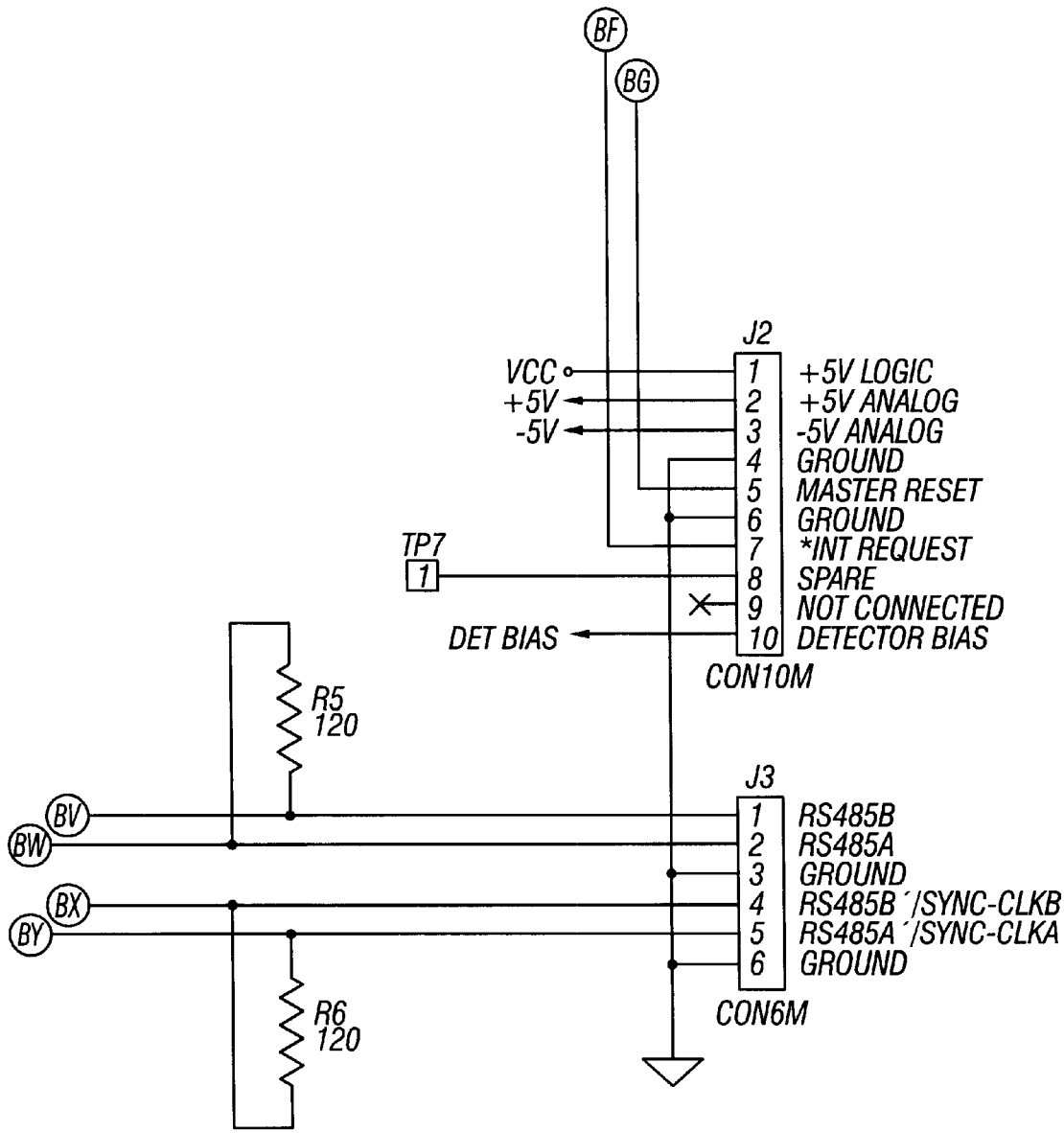
FIG. 8 is a diagram illustrating a preferred screen layout for the image displayed on the display device of FIG. 2.
Figures 1, 5B:
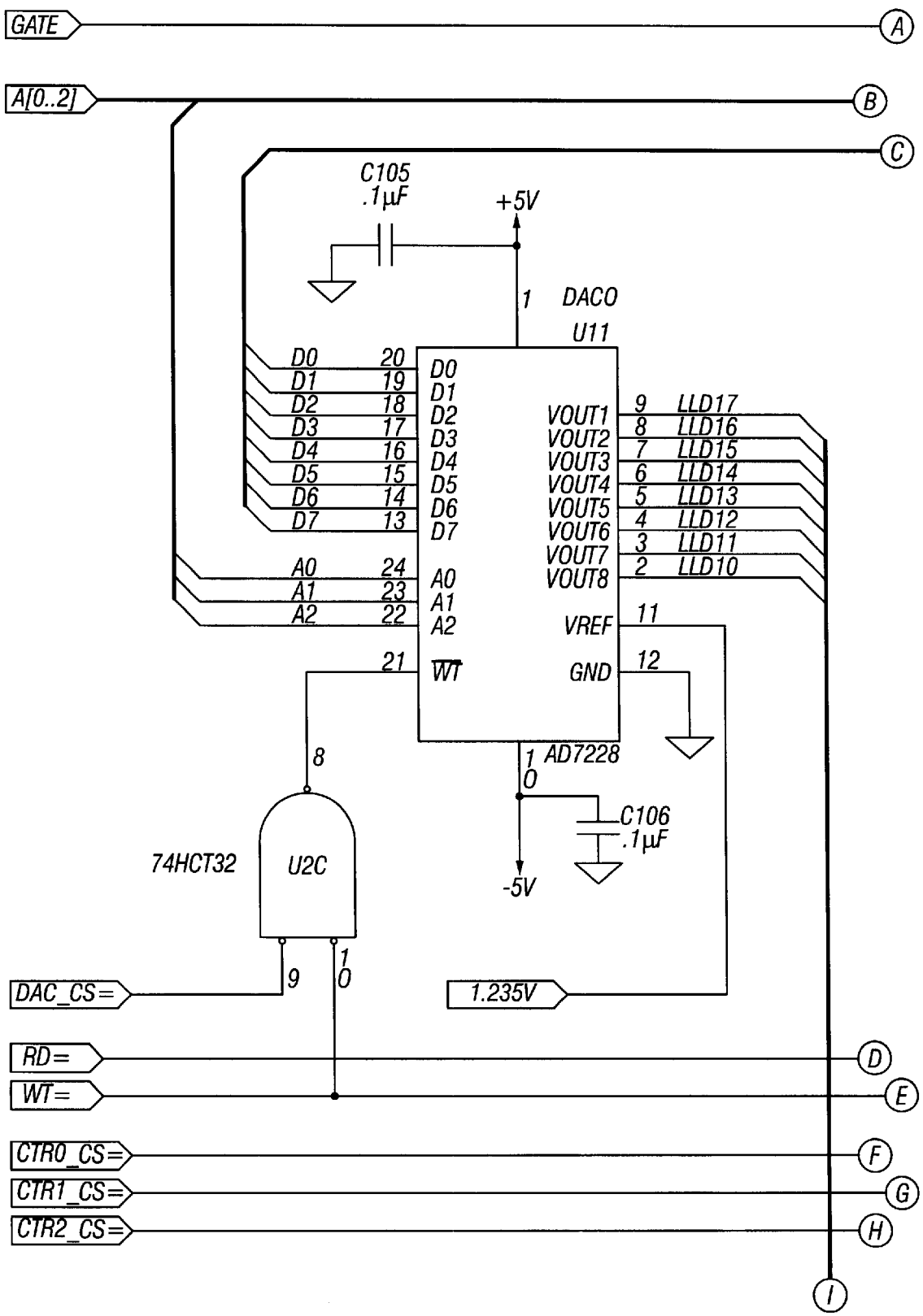
Figures 2, 5B:
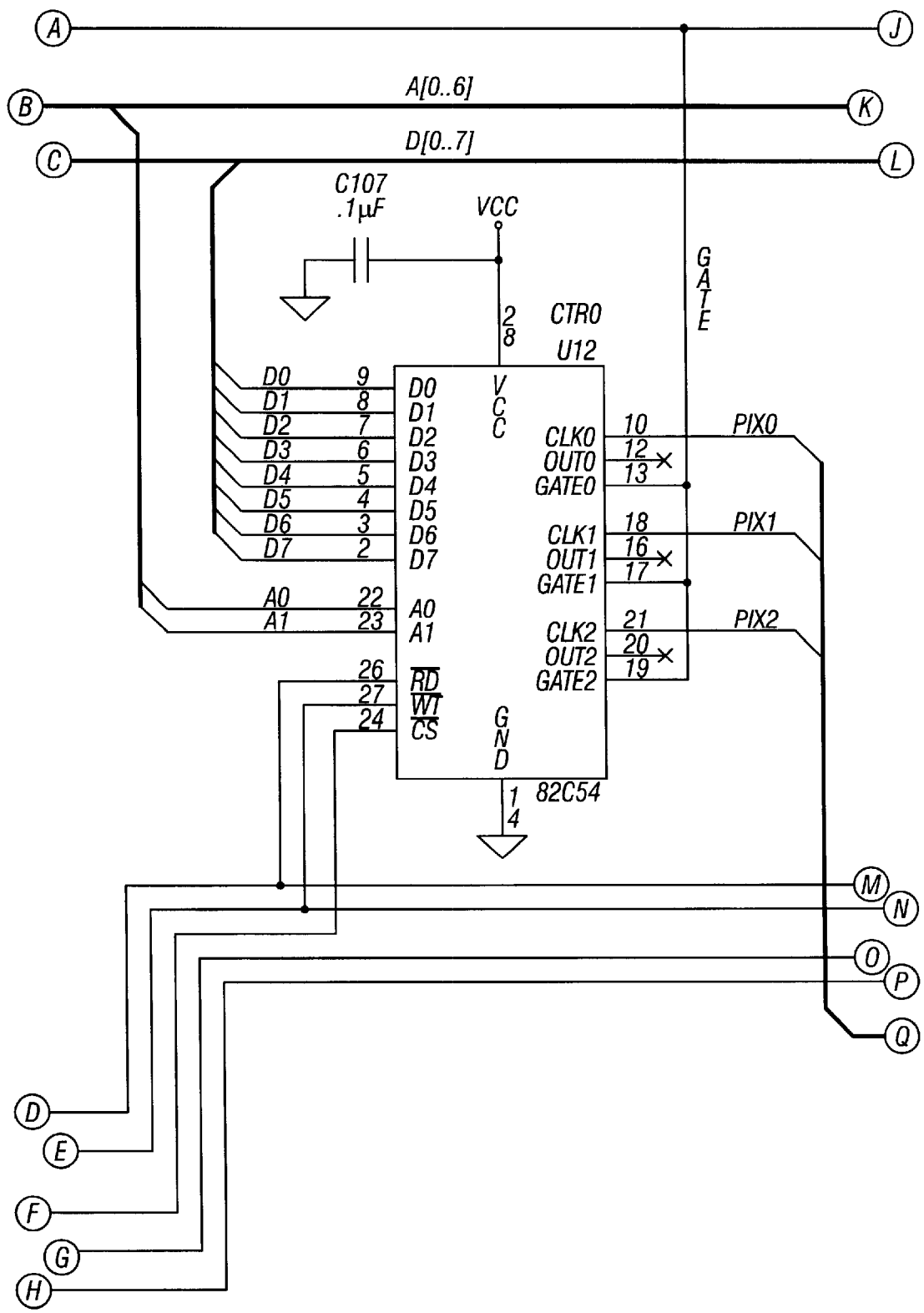
Figures 3, 5B:
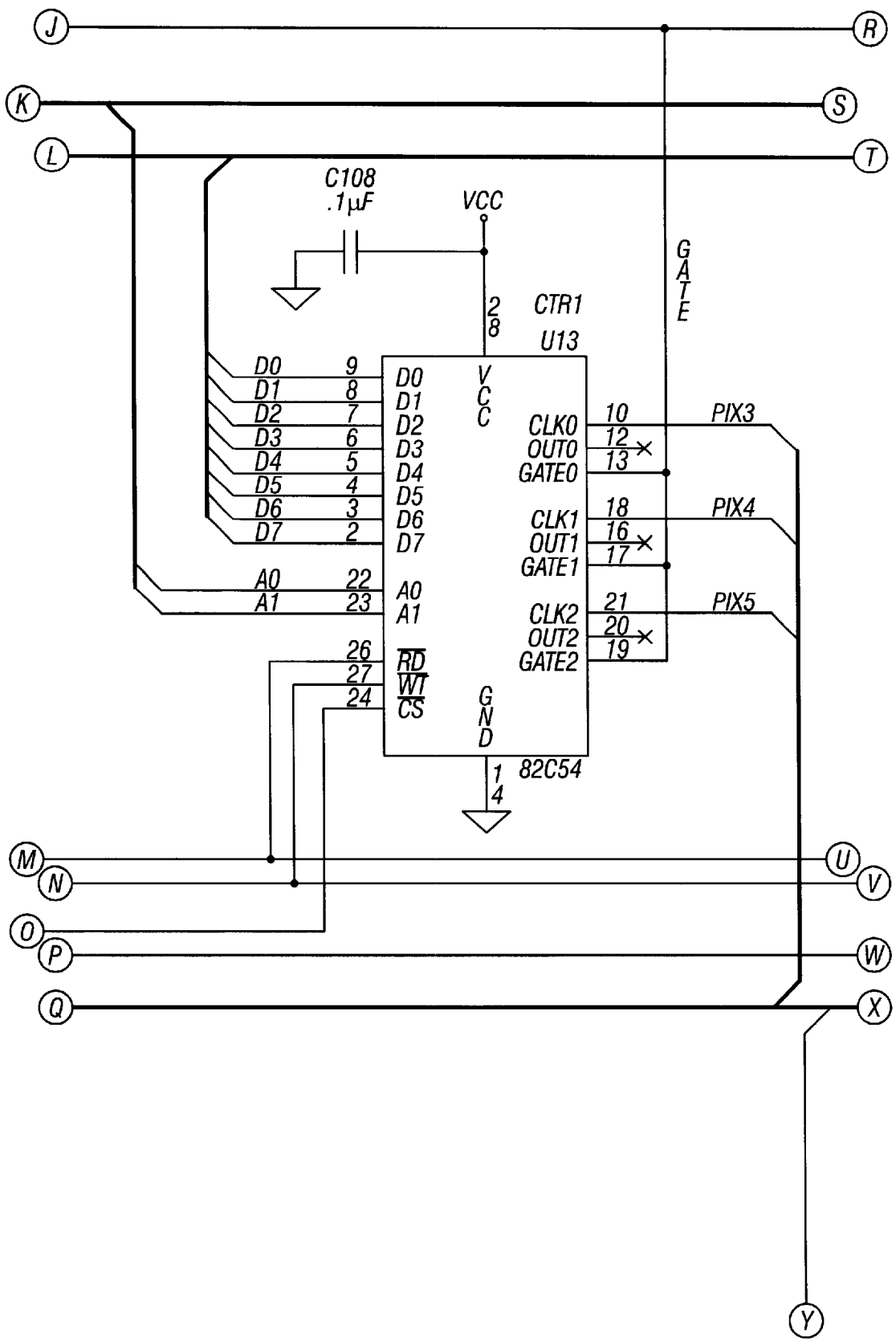
Figures 4, 5B:
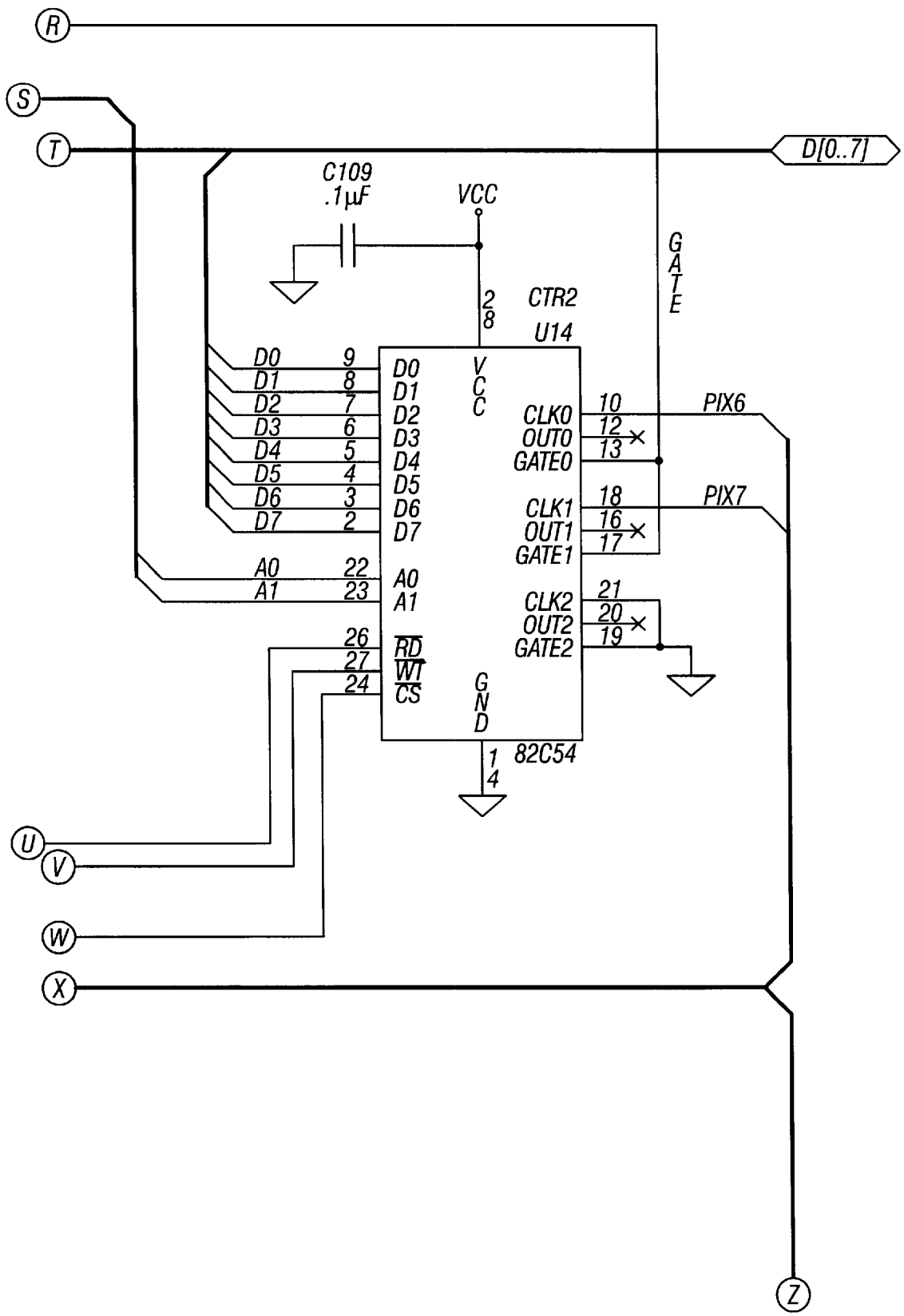
Figures 5, 5B:
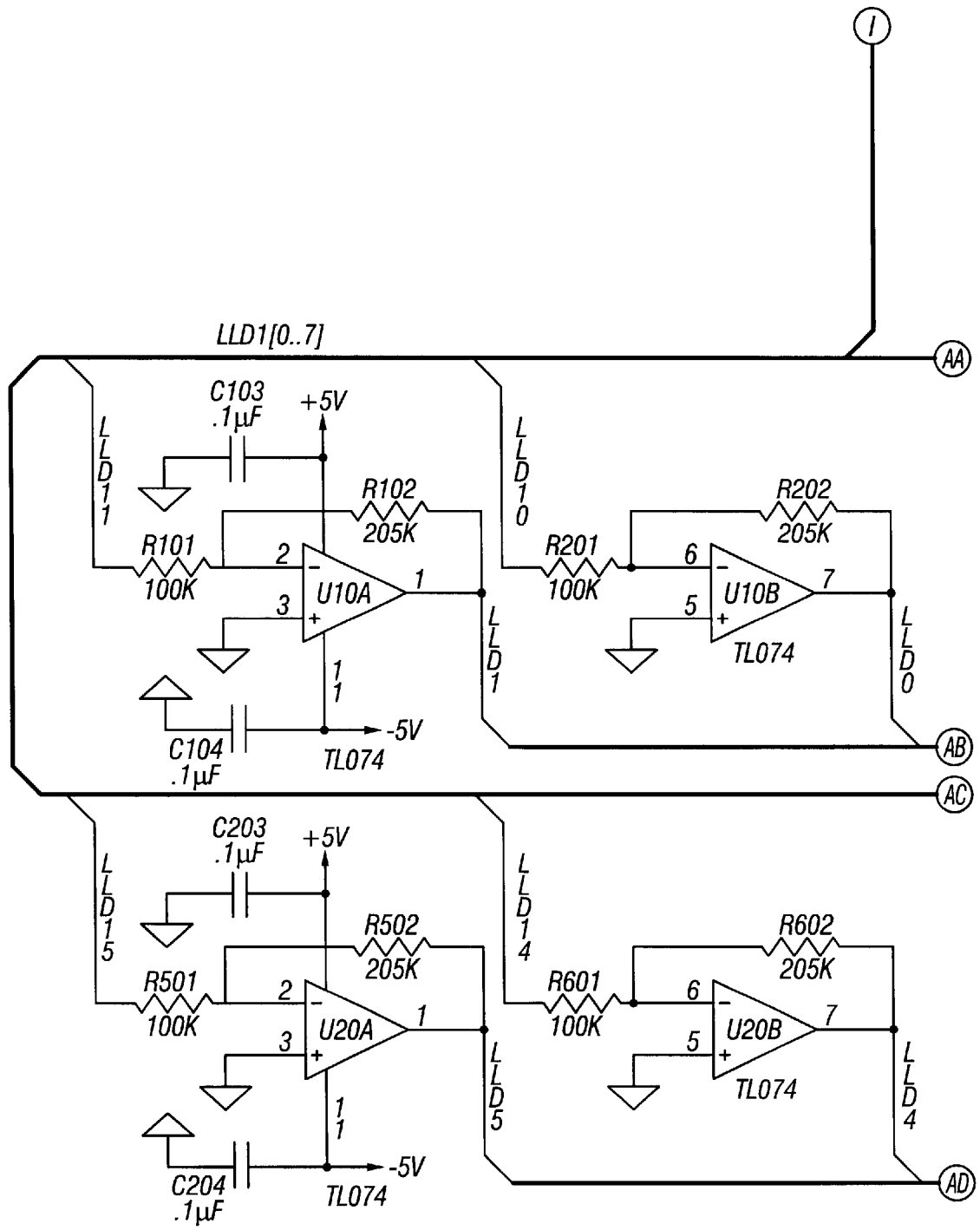
Figures 5, 5B, 6:
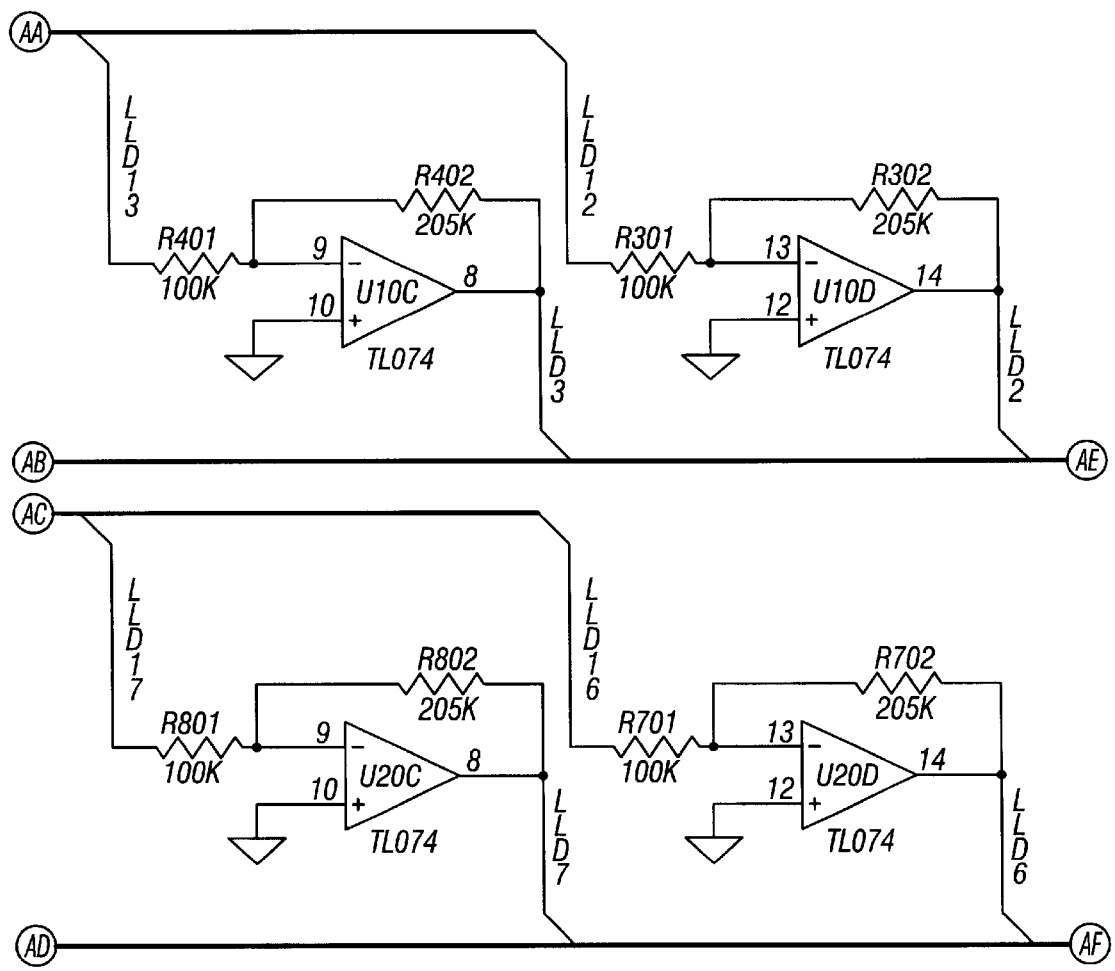
Figures 5, 5B, 6, 7:
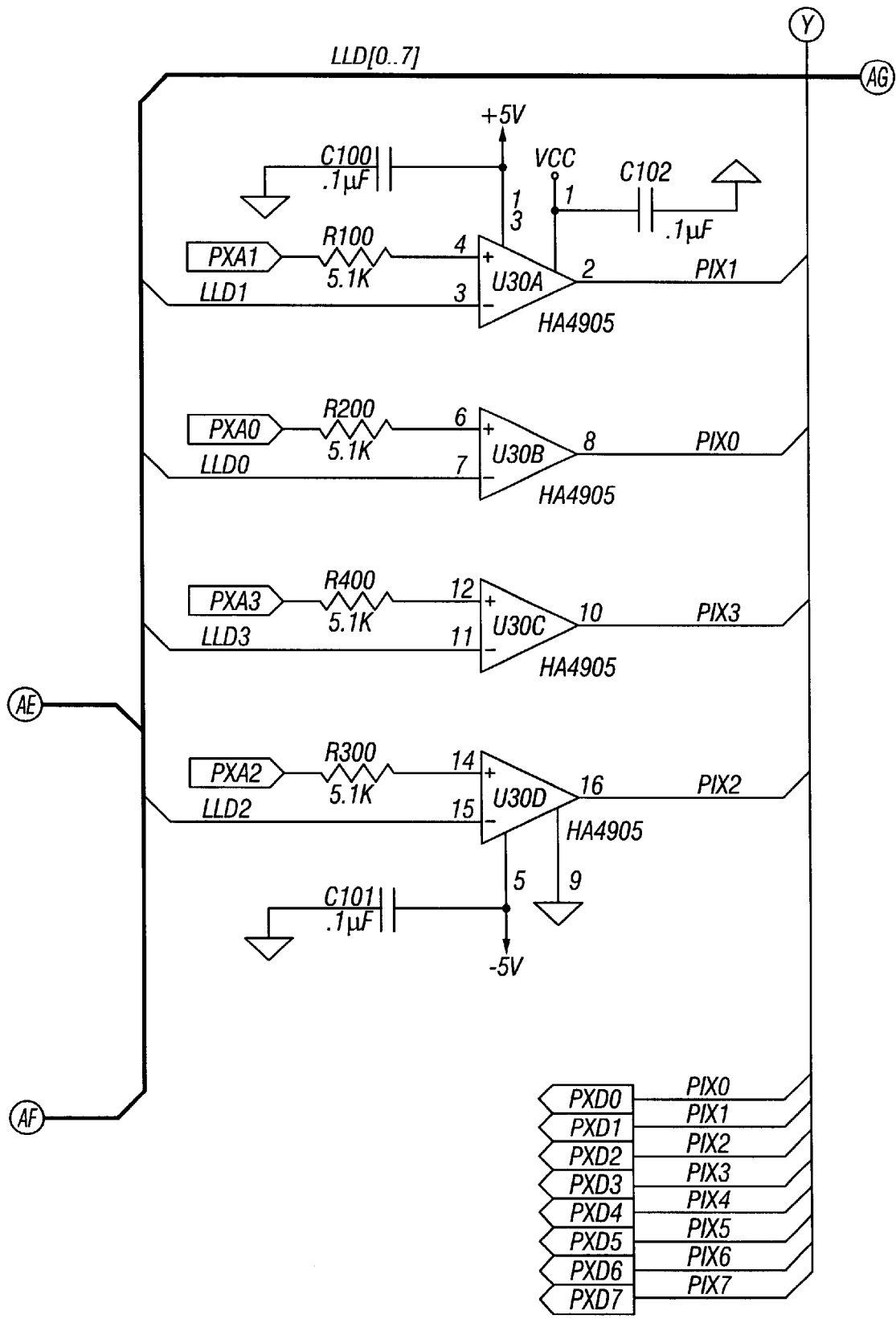
Figures 5, 5B, 6, 7, 8:
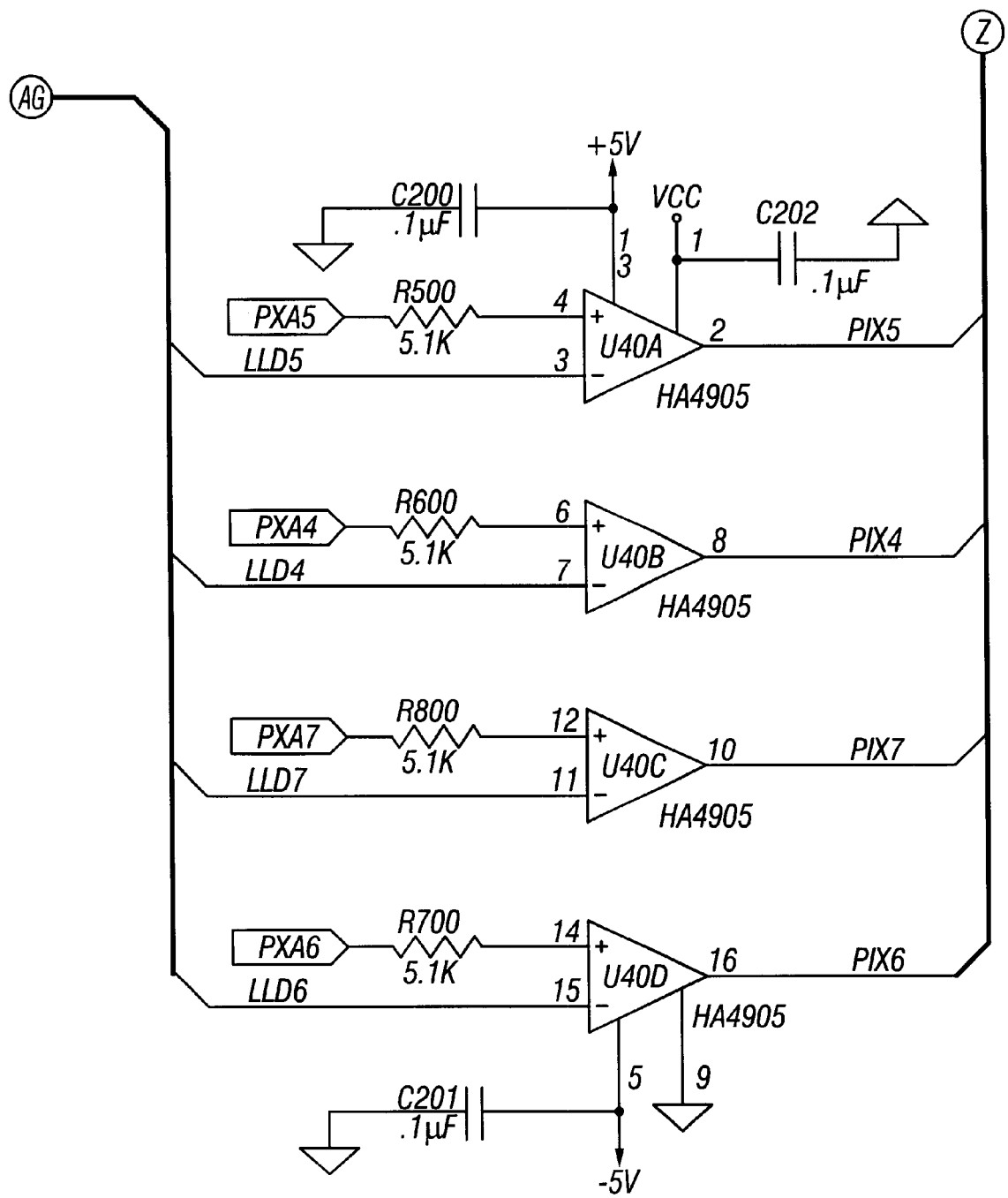
Figures 1, 5C:
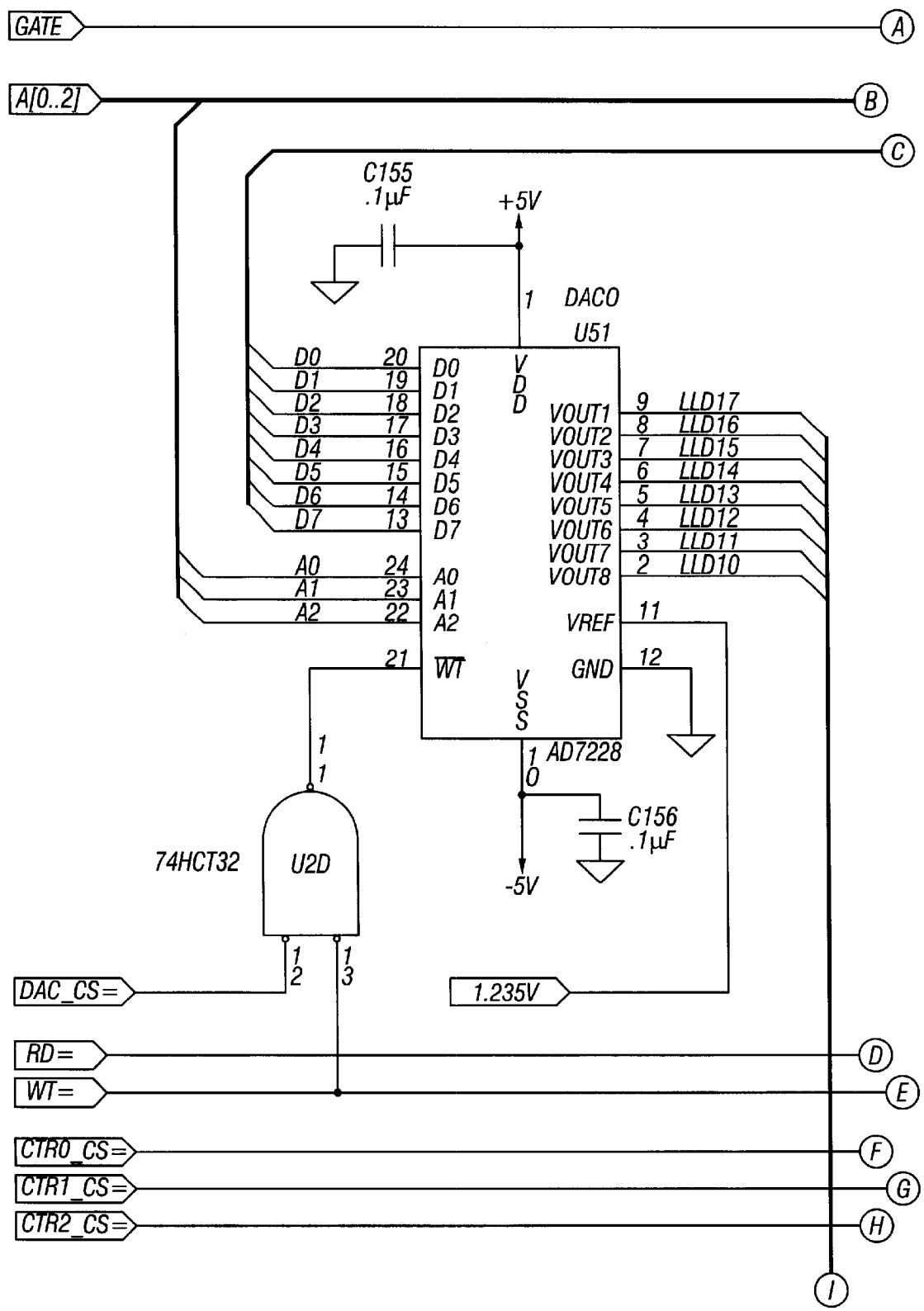
Figures 2, 5C:
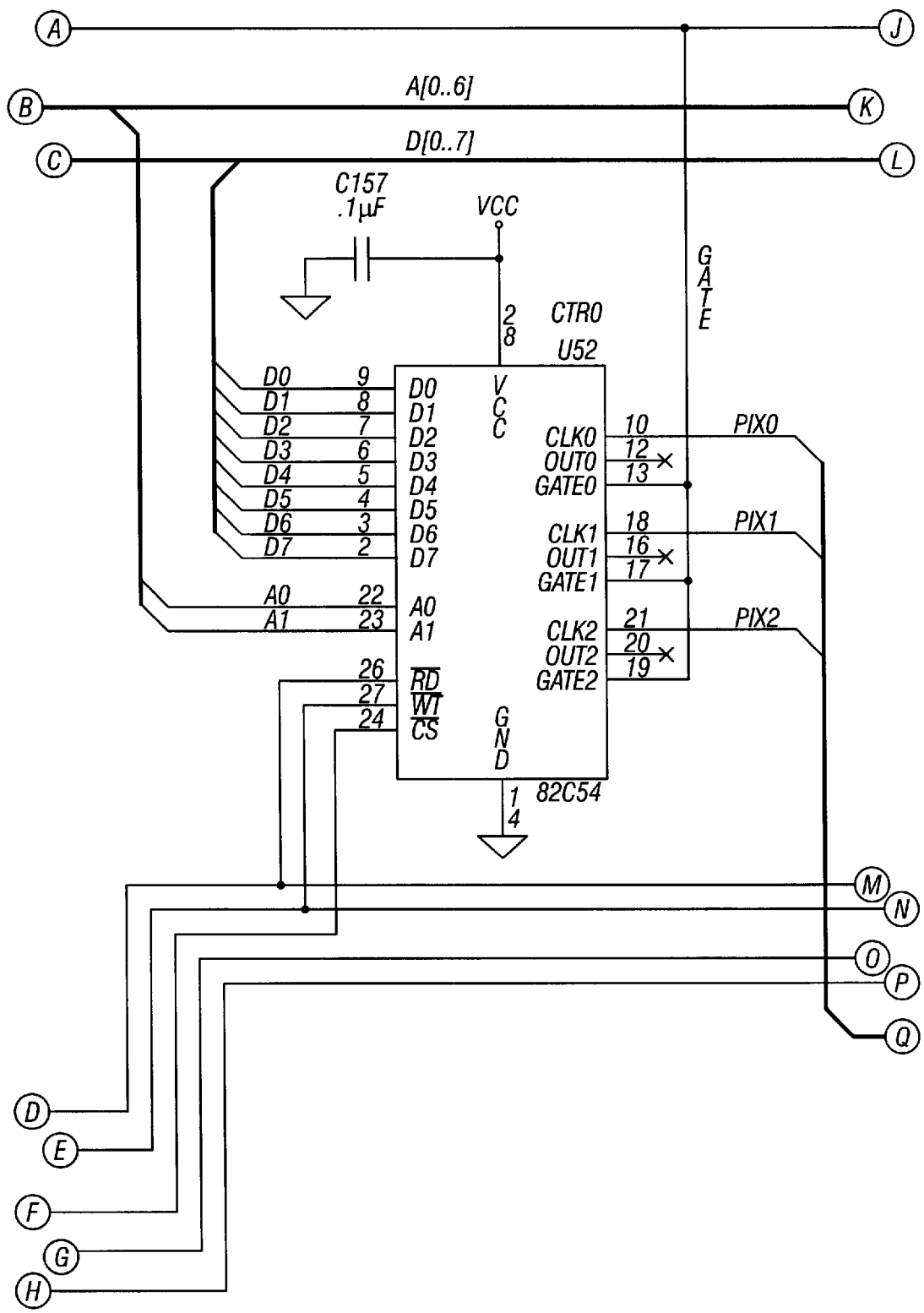
Figures 3, 5C:
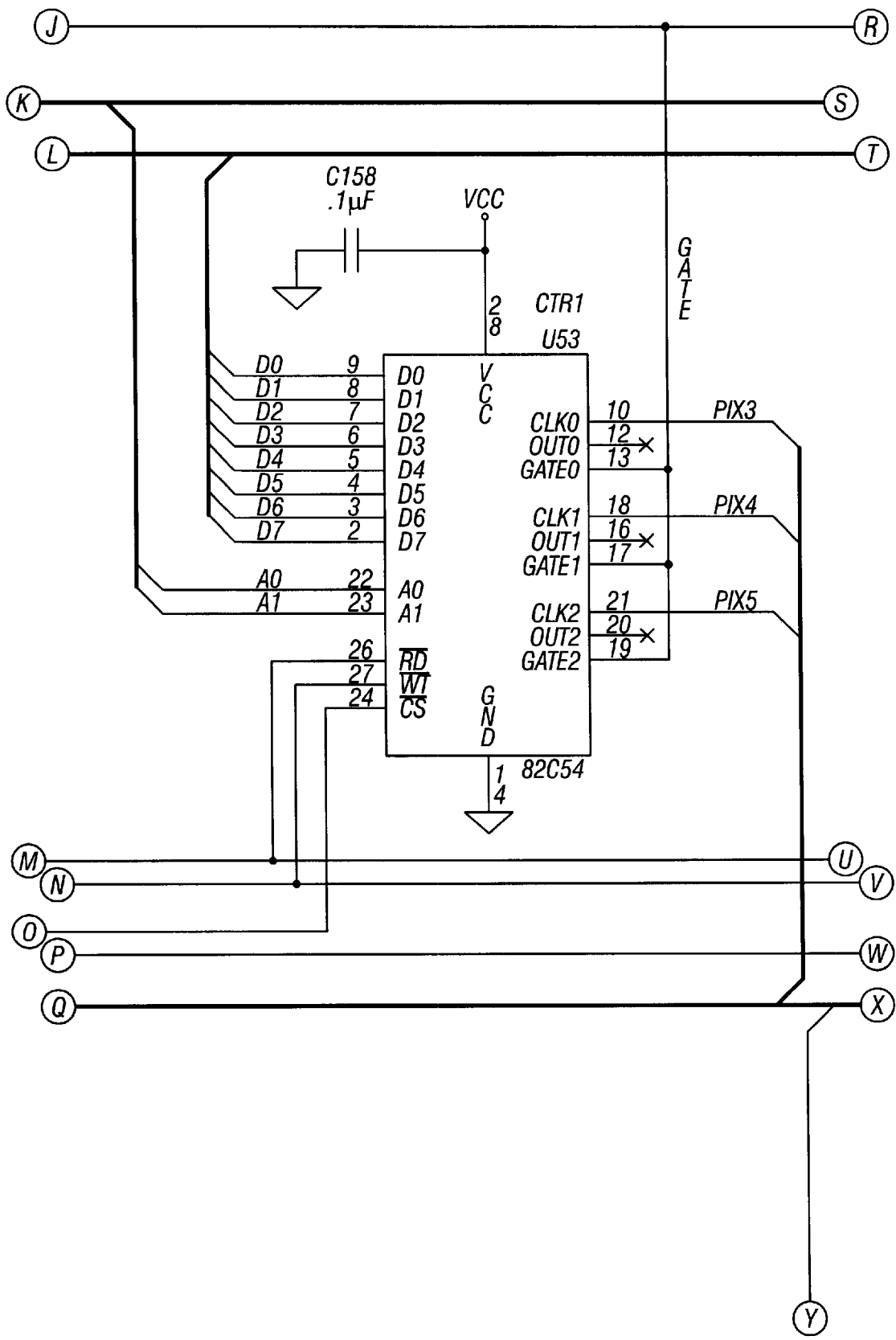
Figures 4, 5C:
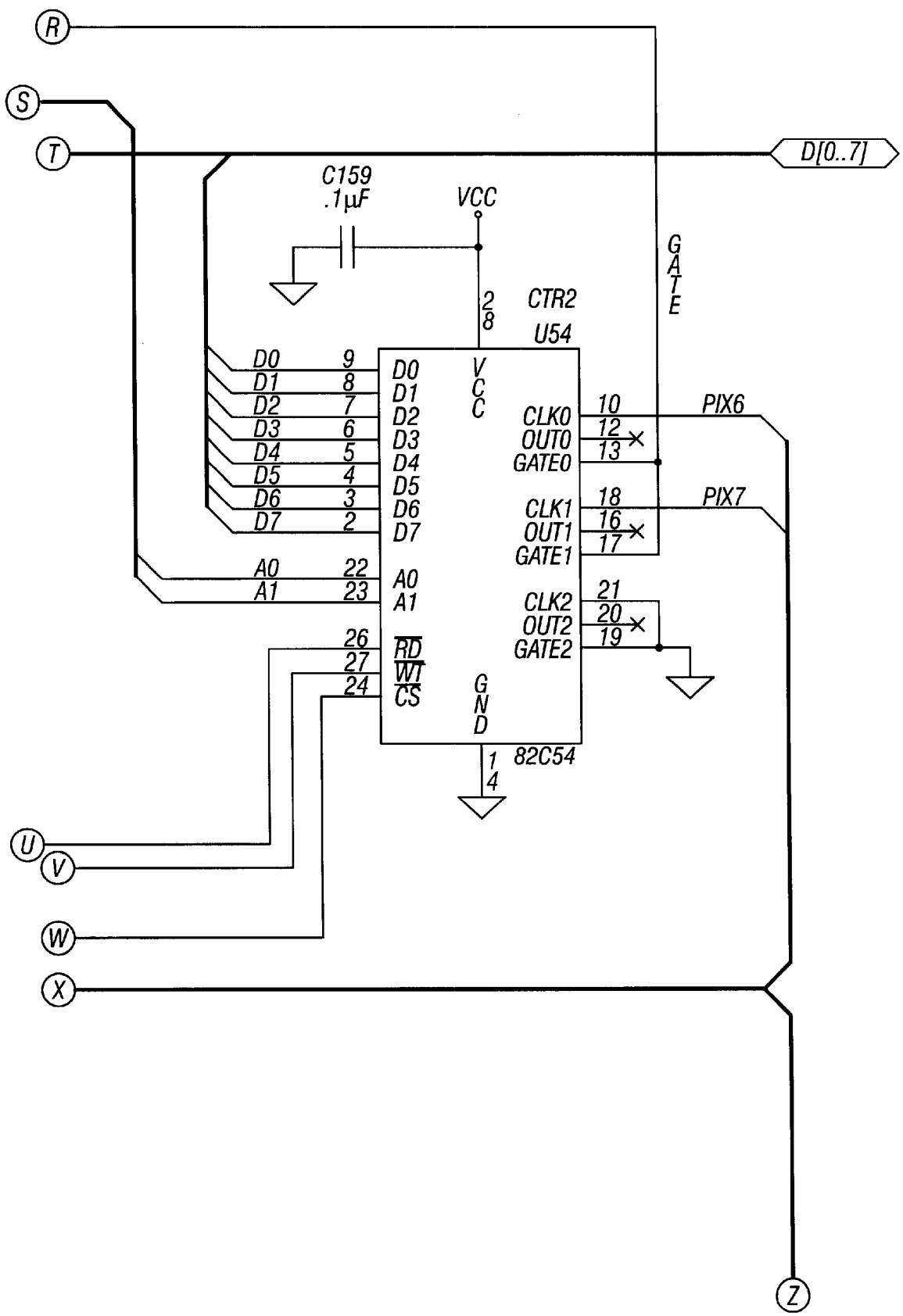
Figures 5, 5C:
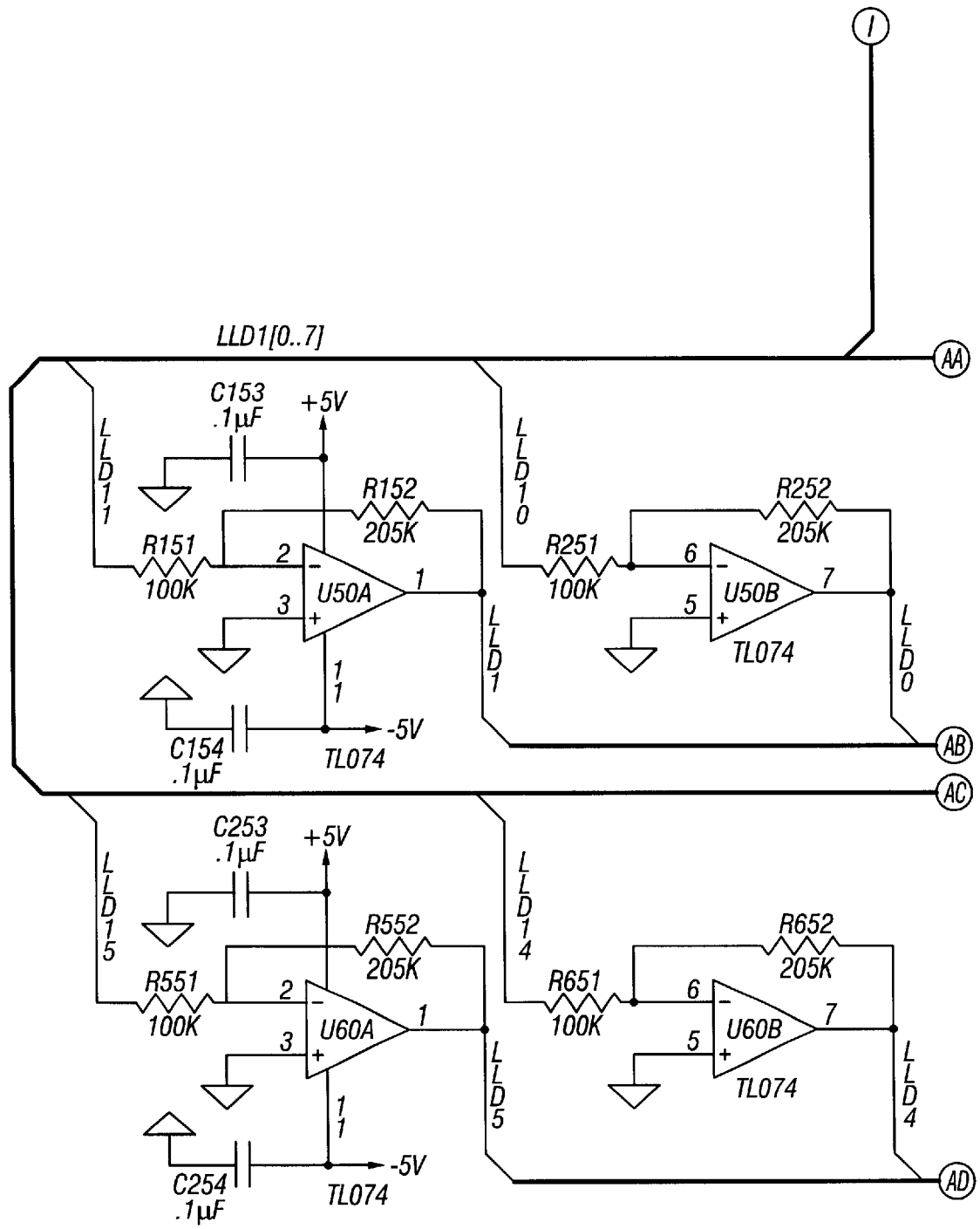
Figures 5, 5C, 6:
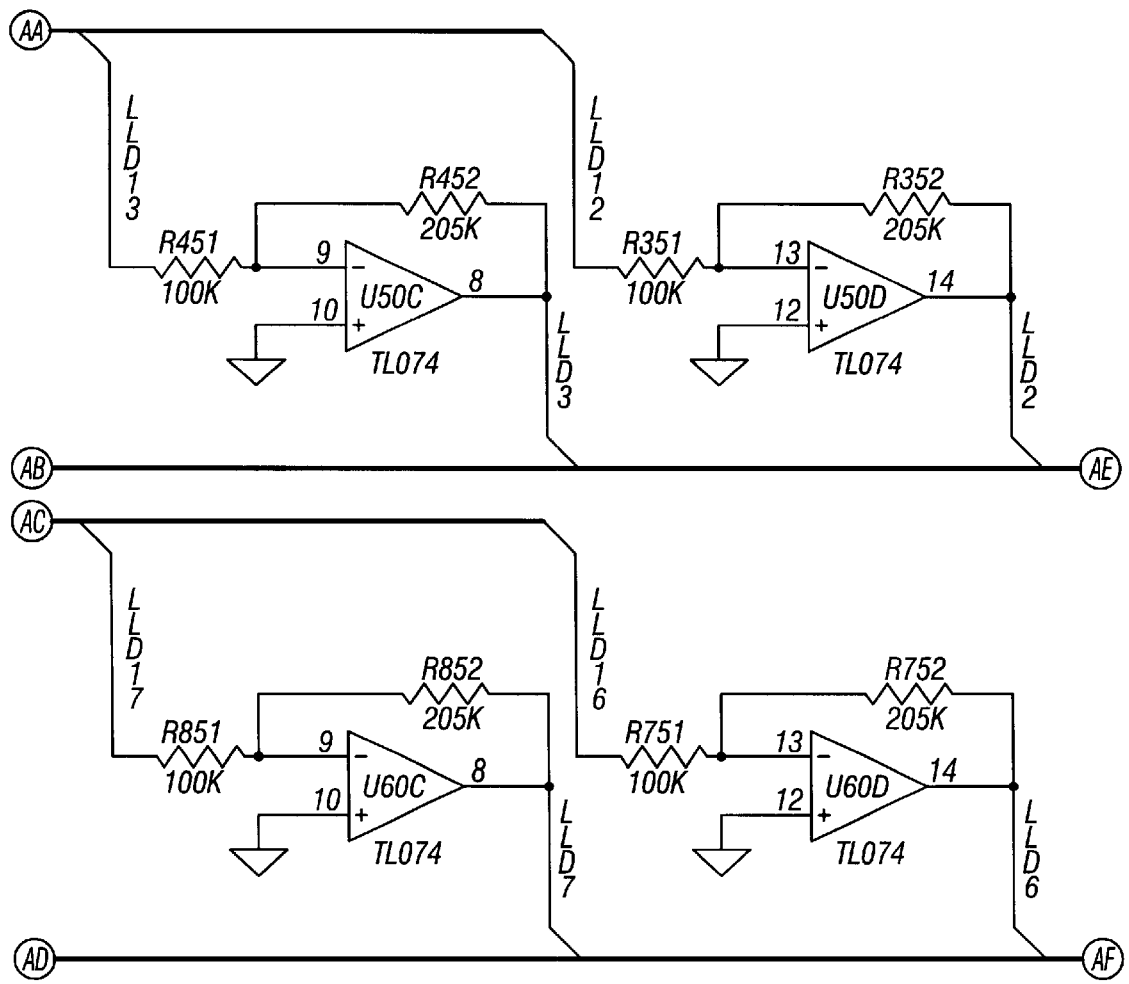
Figures 5, 5C, 6, 7:
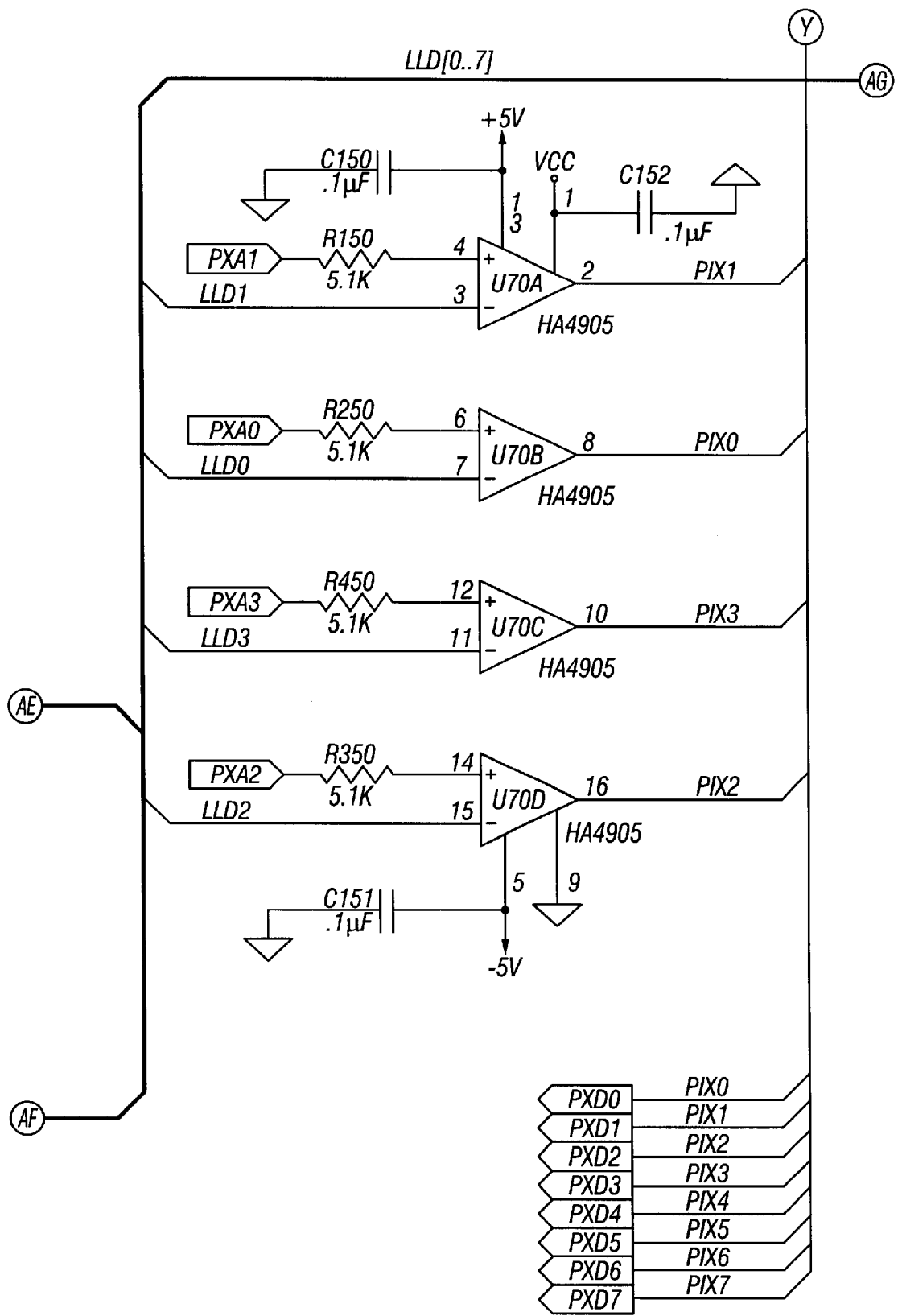
Figures 5, 5C, 6, 7, 8:
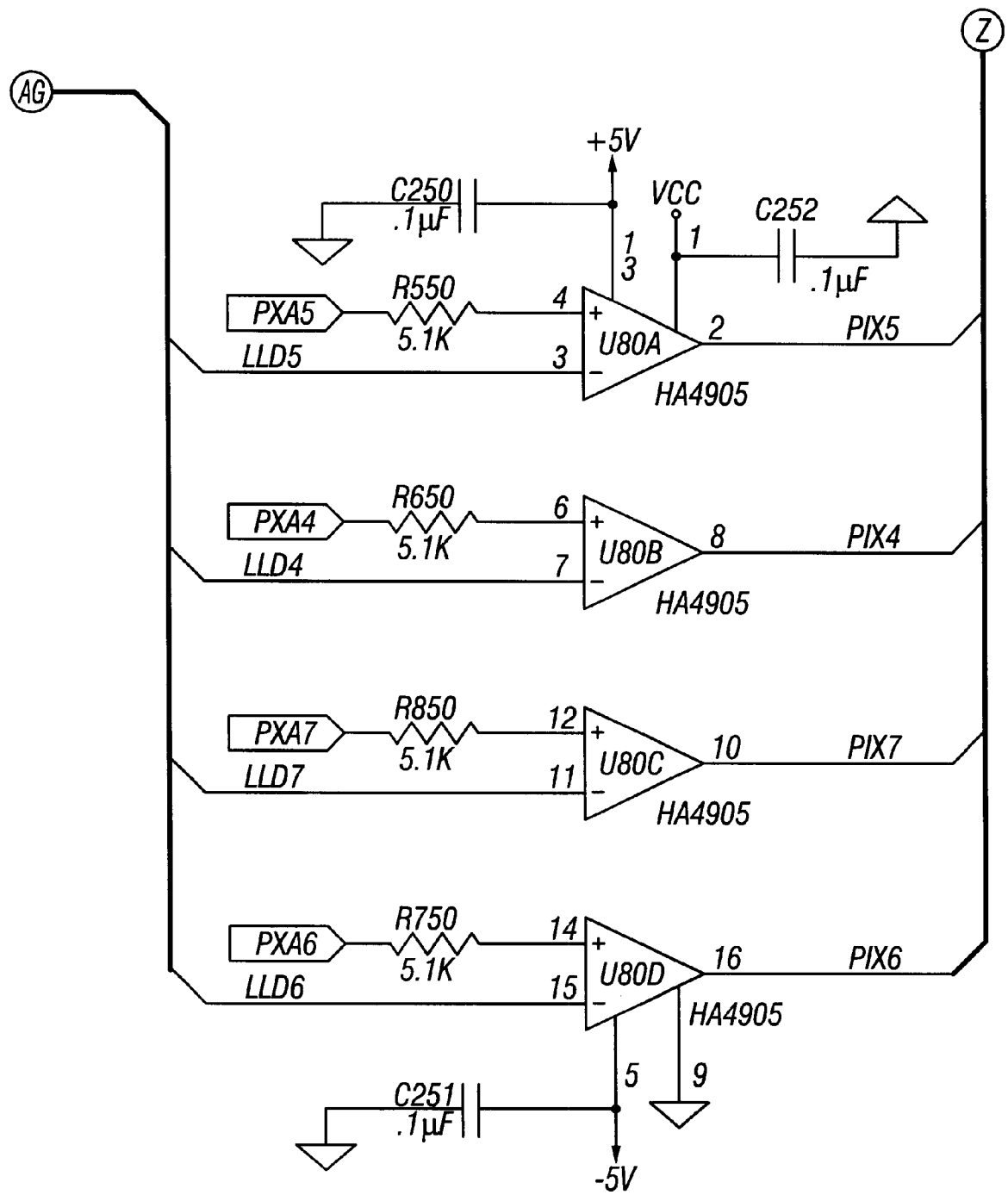
Figure 6:
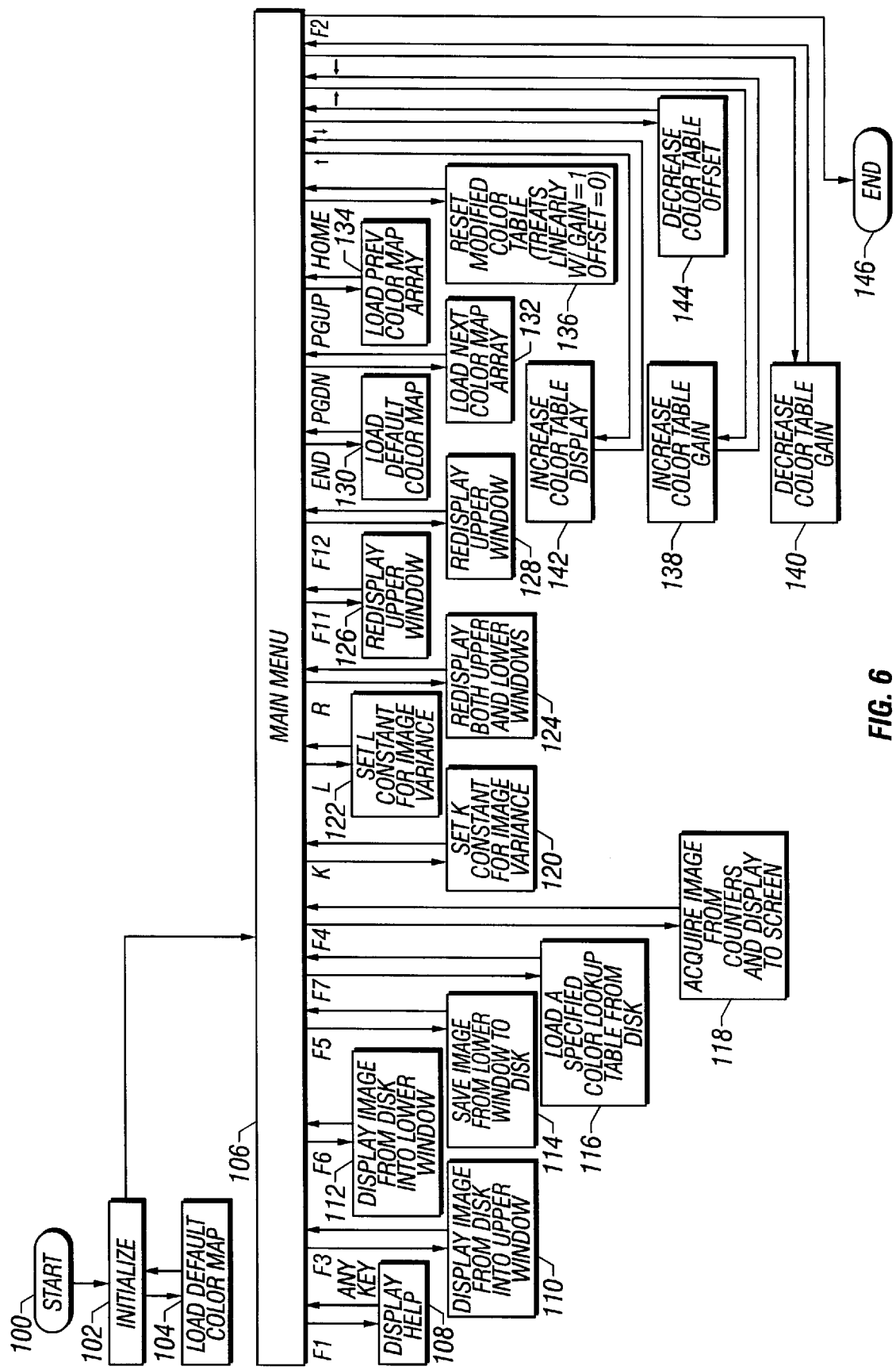
Figure 7:
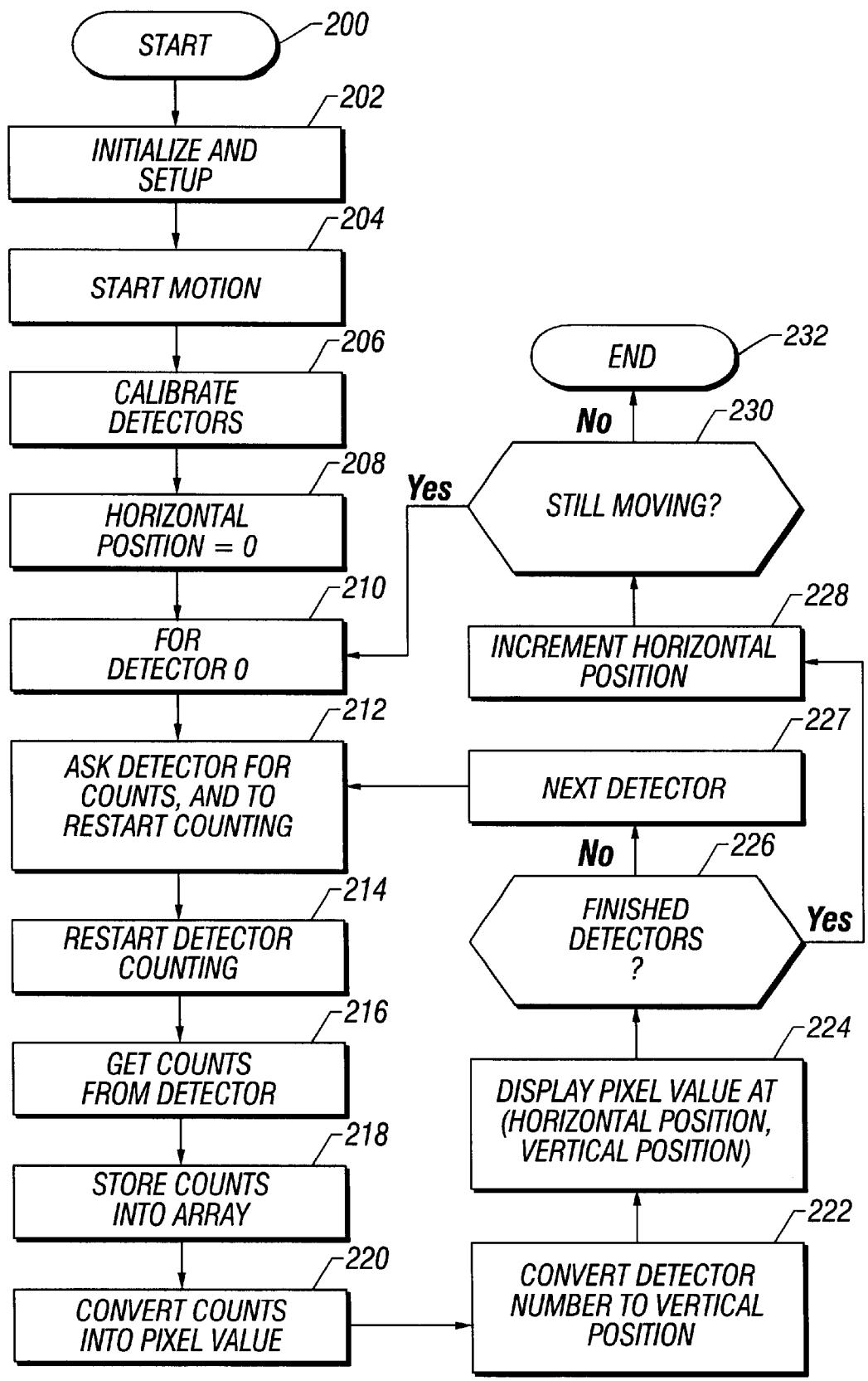
Figure 8:
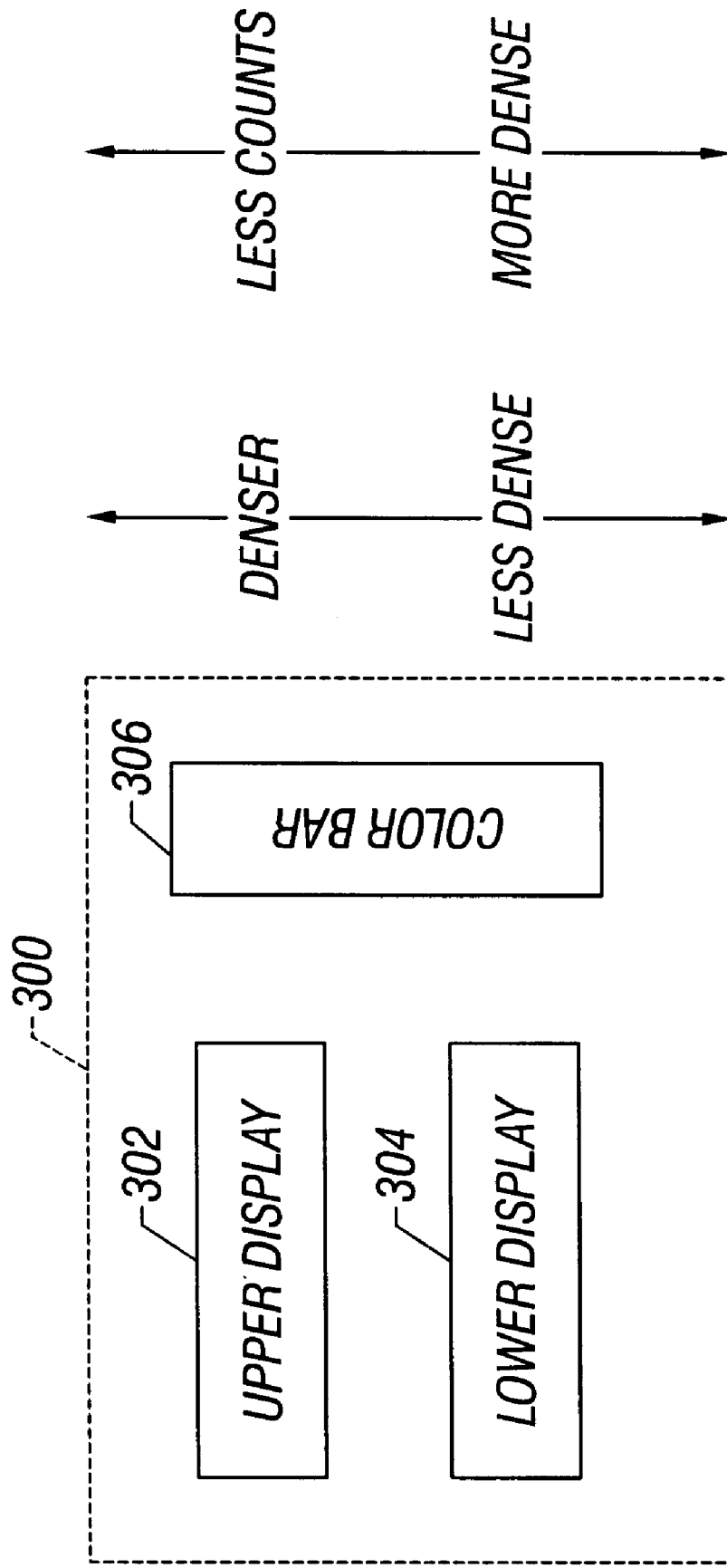

Referring next to FIGS. 5A, 5B and 5C, a schematic diagram is shown one variation of a digital portion of the 16-channel processing units of FIGS. 2 and 3. The schematics of FIGS. 5A, 5B and 5C are self-explanatory to one of skill in the art and therefore further explanation of these figures is not made herein.

Figures 1, 4A:
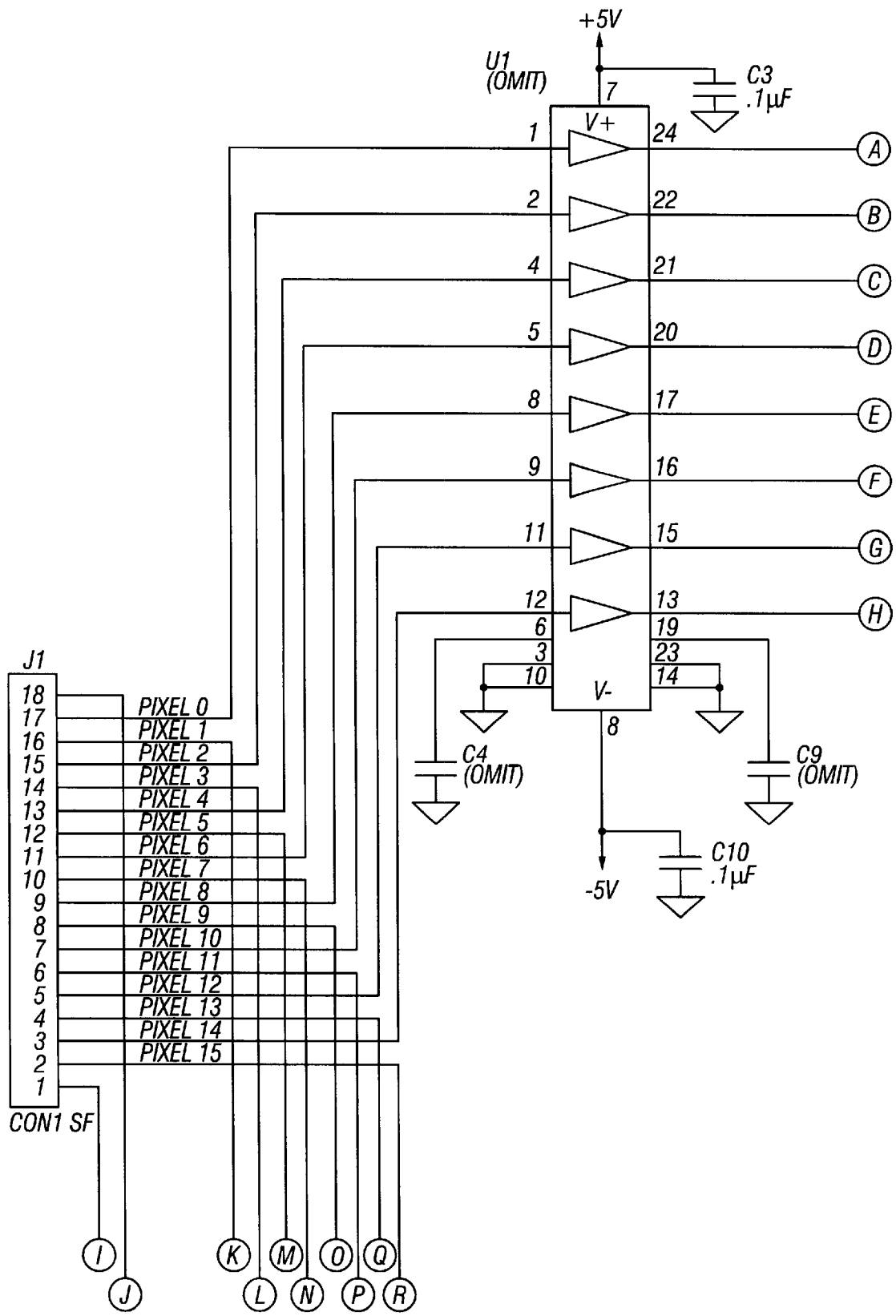
FIGS. 4A, 4B, 4C, 4D, 4E, 4F, 4G, 4H and 4I are a schematic diagram showing one variation of an analog portion the 16-channel processing units of FIGS. 2 and 3.
Figures 2, 4A:
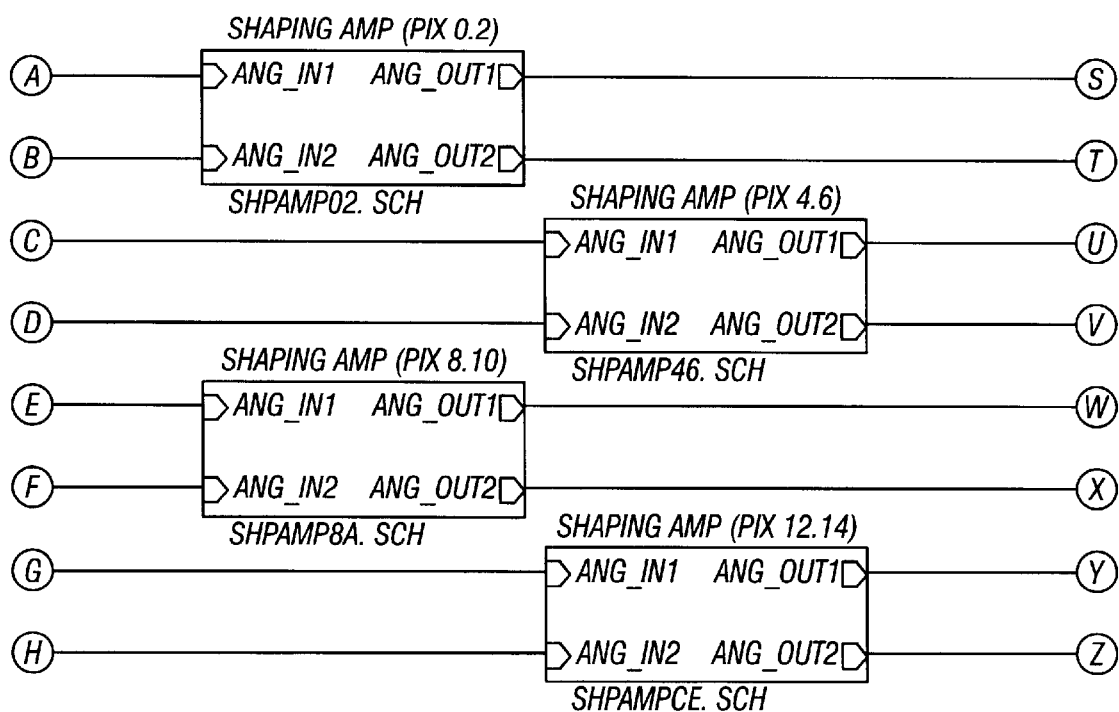
Figures 3, 4A:
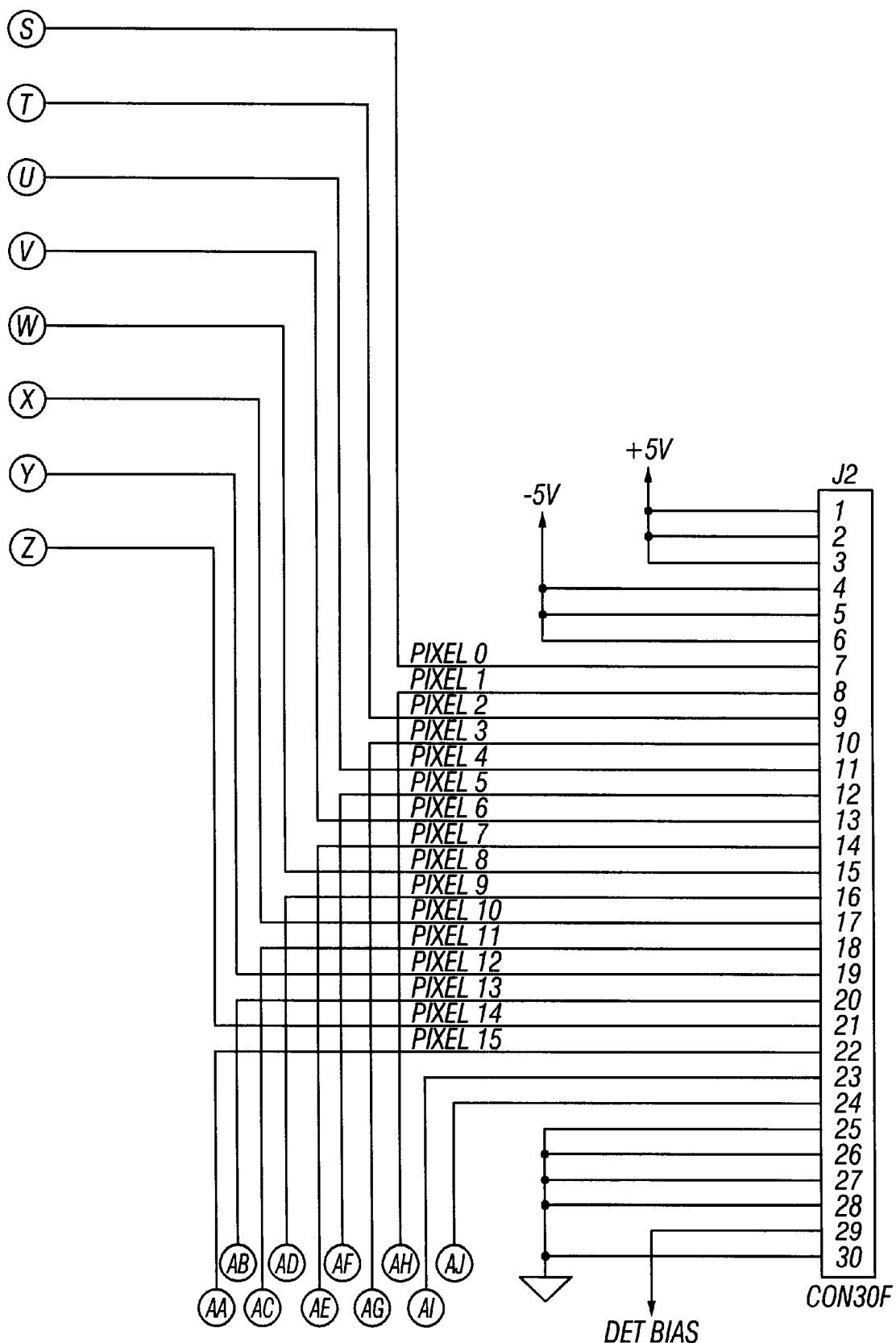
Figures 4, 4A:
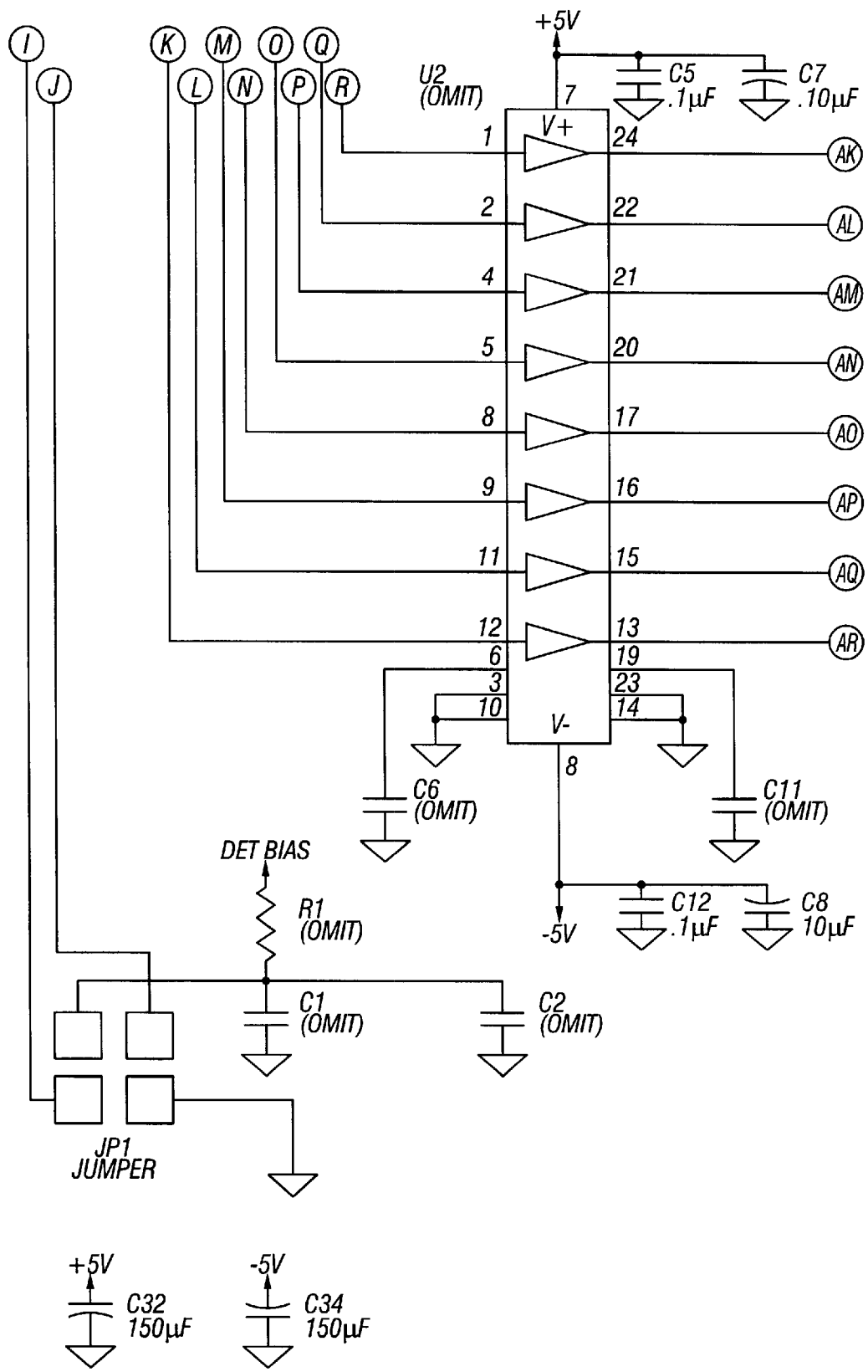
Figures 4, 4A, 5:
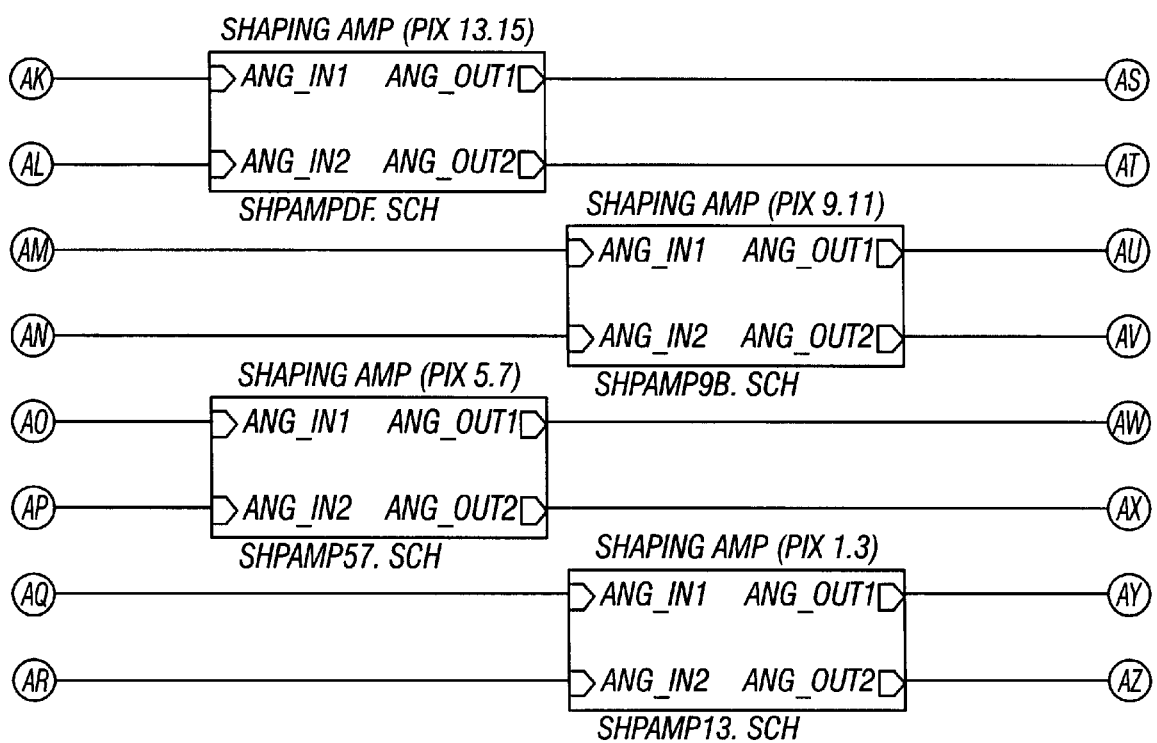
Figures 4, 4A, 5, 6:
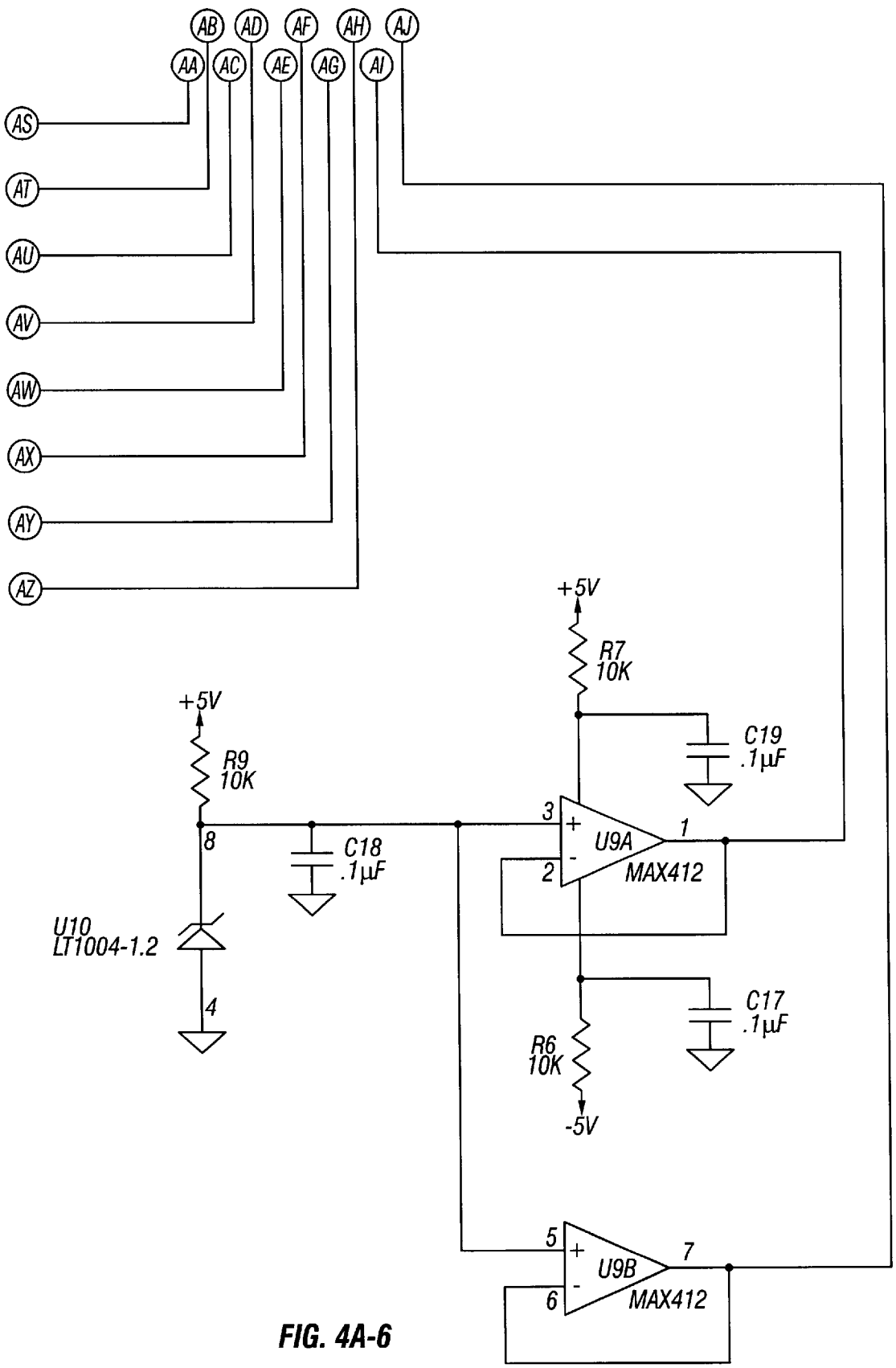
FIG. 6 is a block diagram of functional components that make up one embodiment of a software system with which the computer of FIG. 2 is controlled.
Figure 4B:
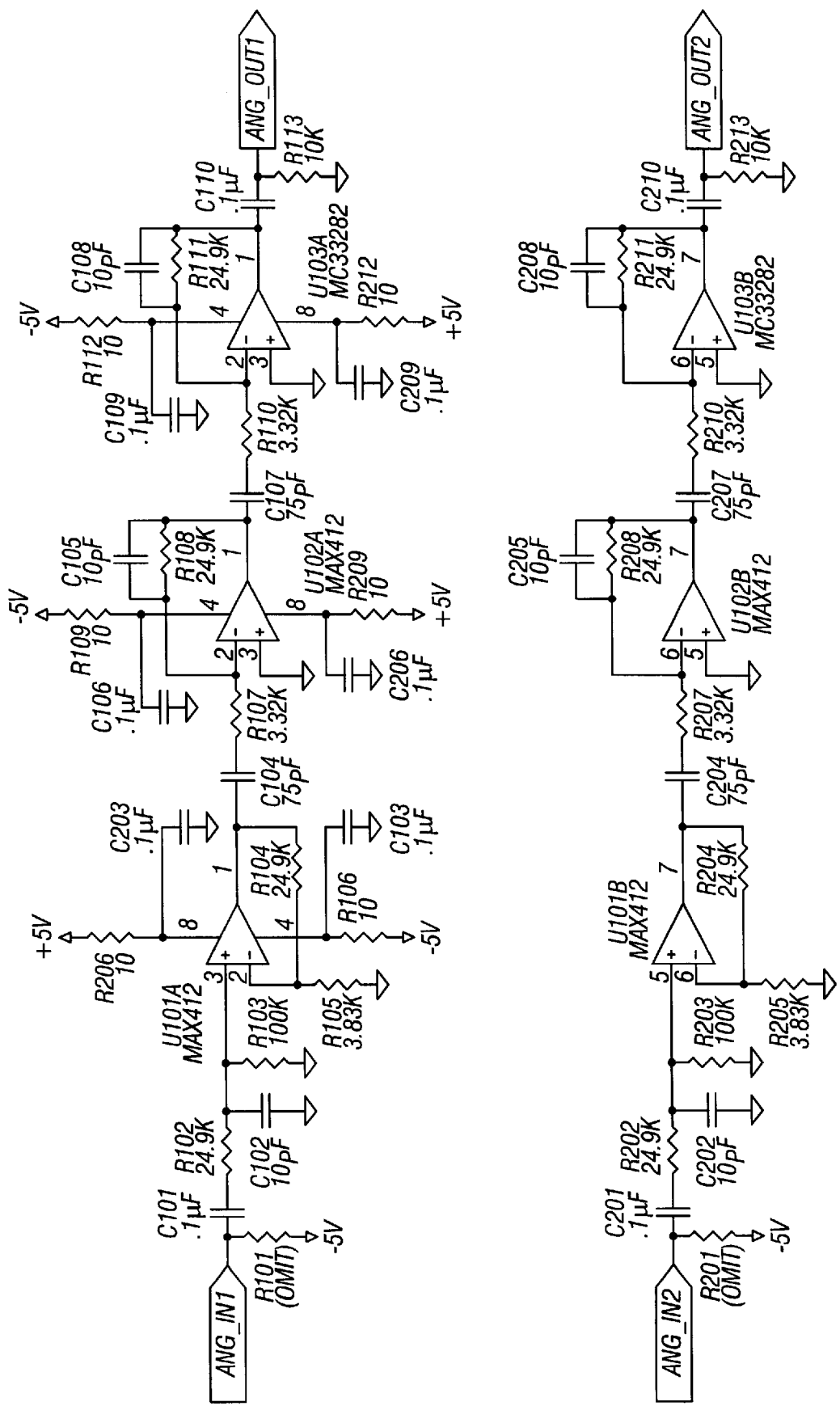
Figure 4C:
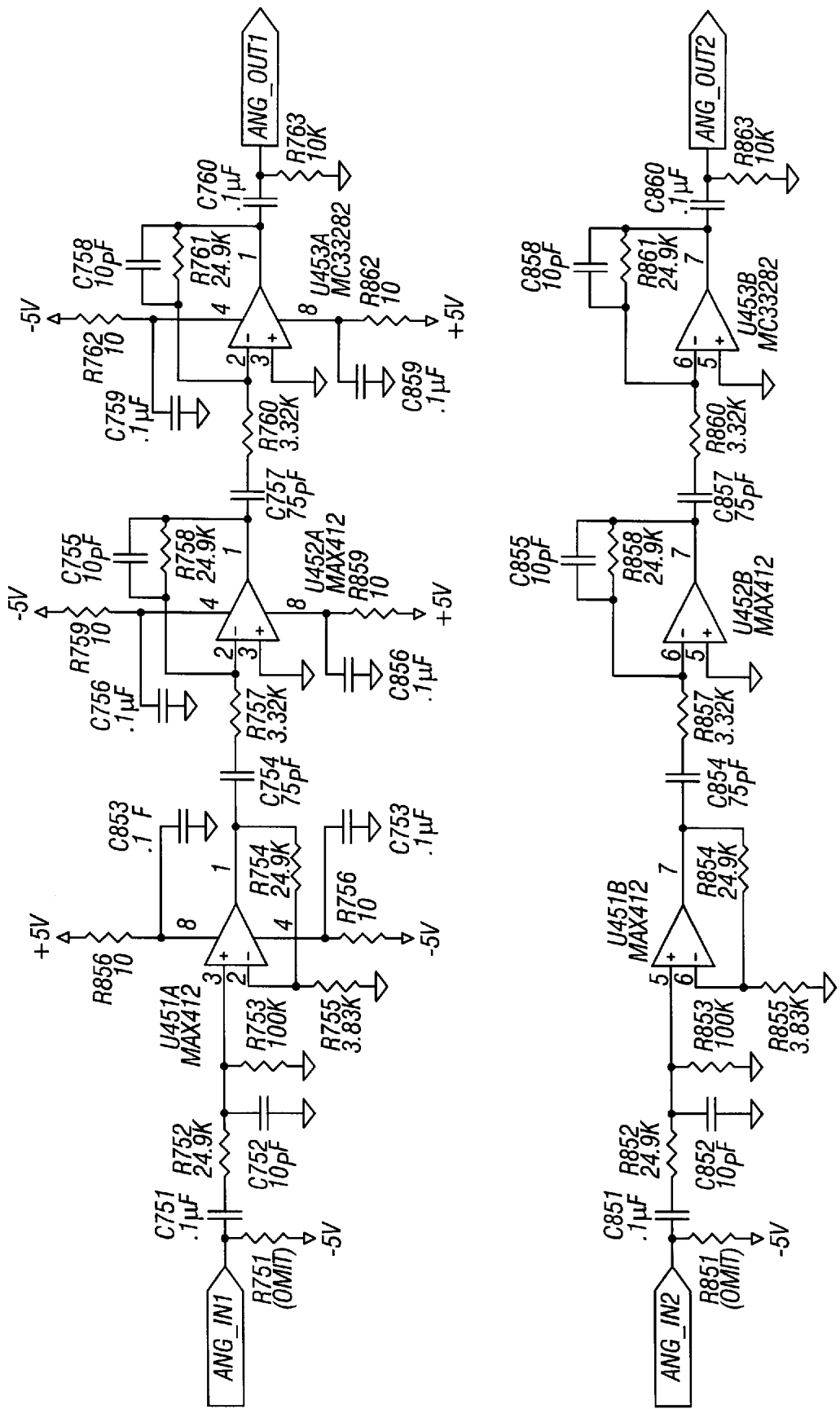
Figure 4D:
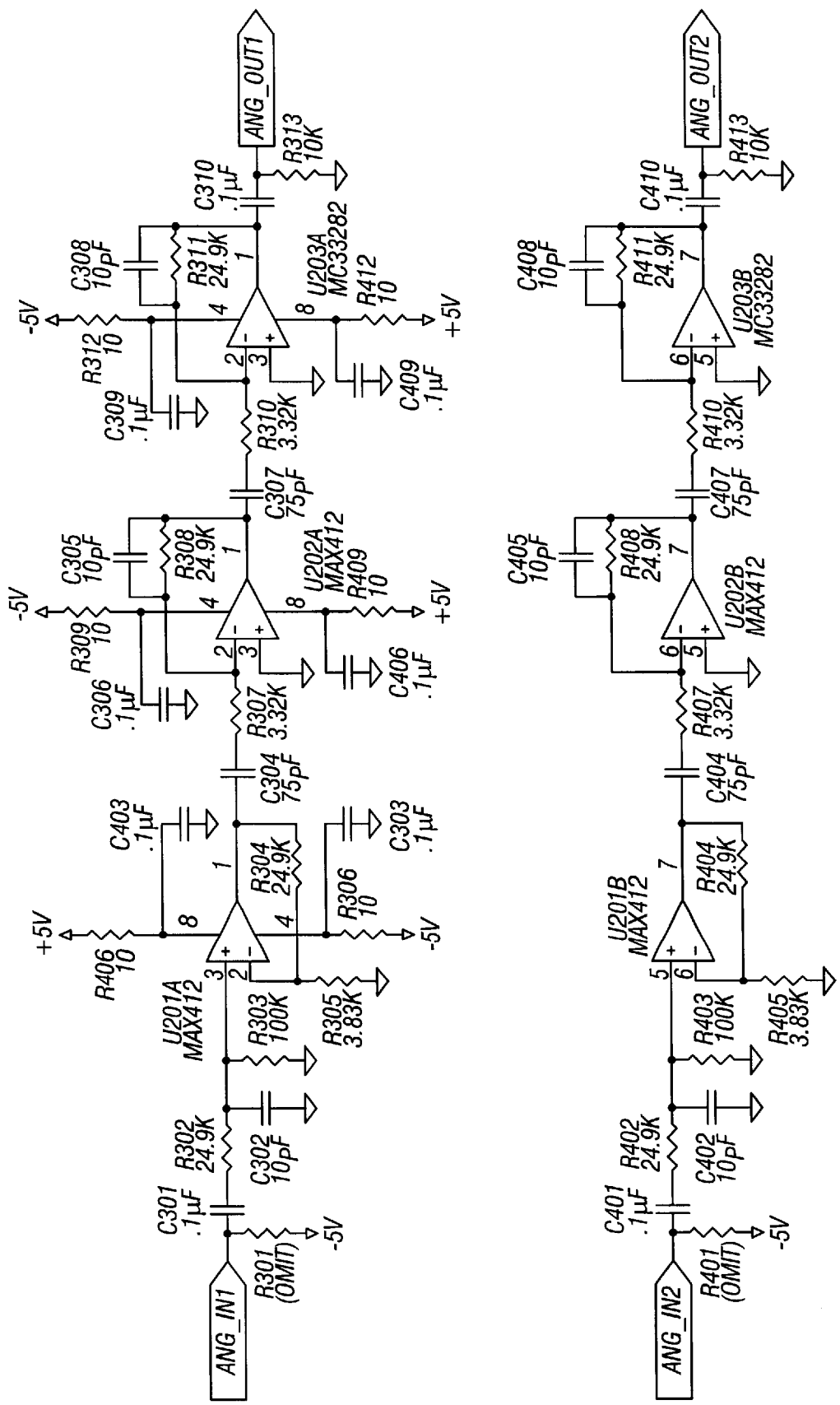
Figure 4E:
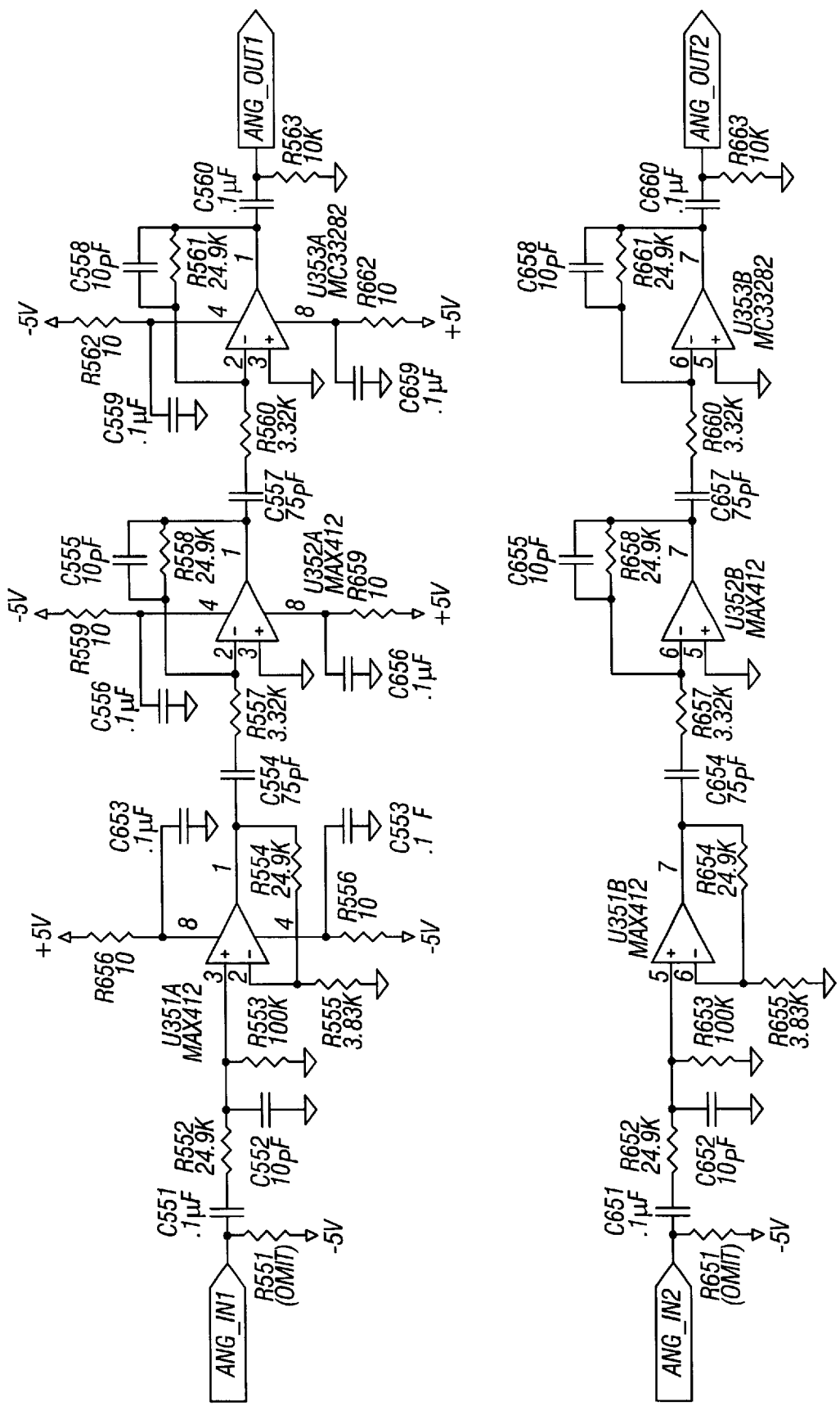
Figure 4F:
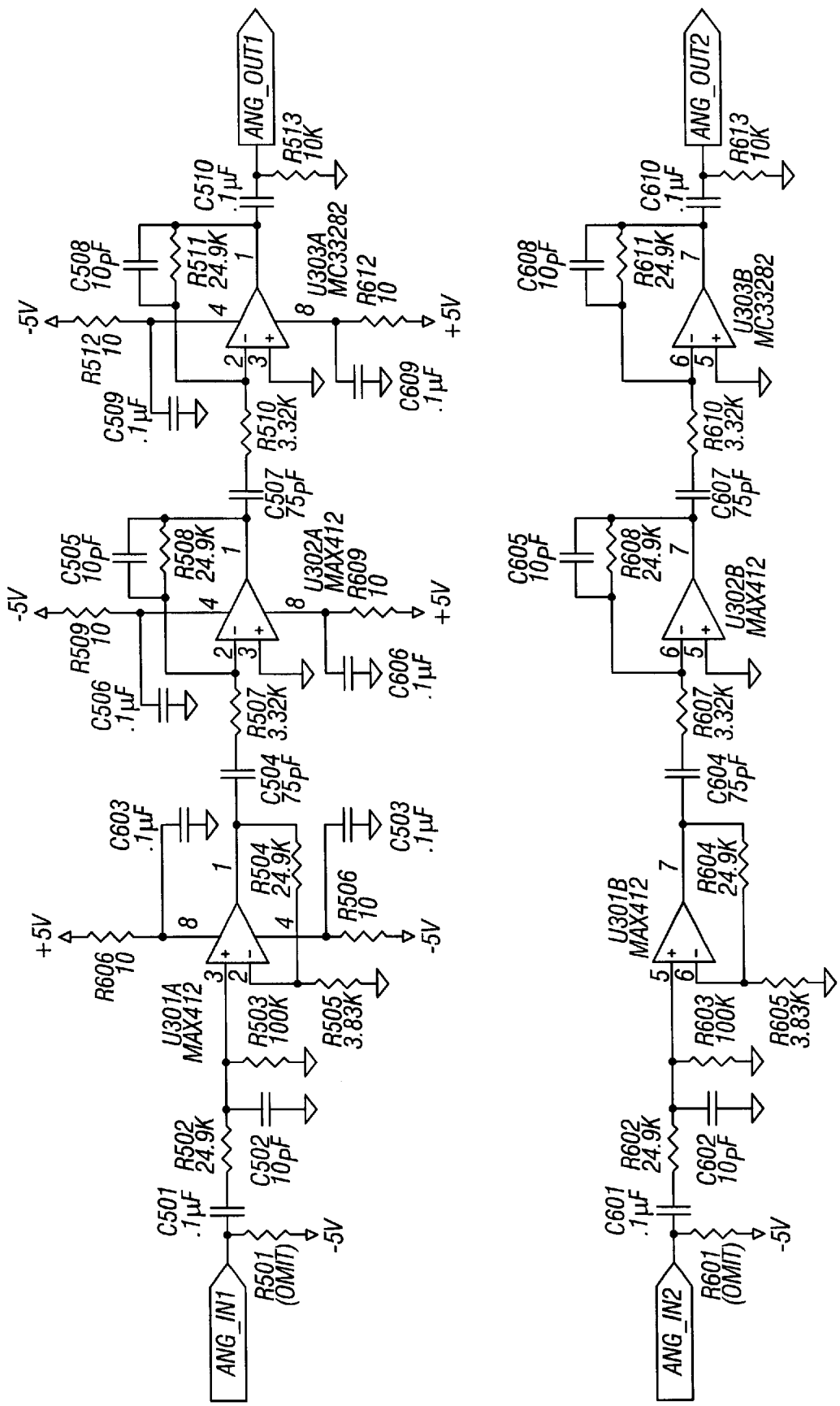
Figure 4G:
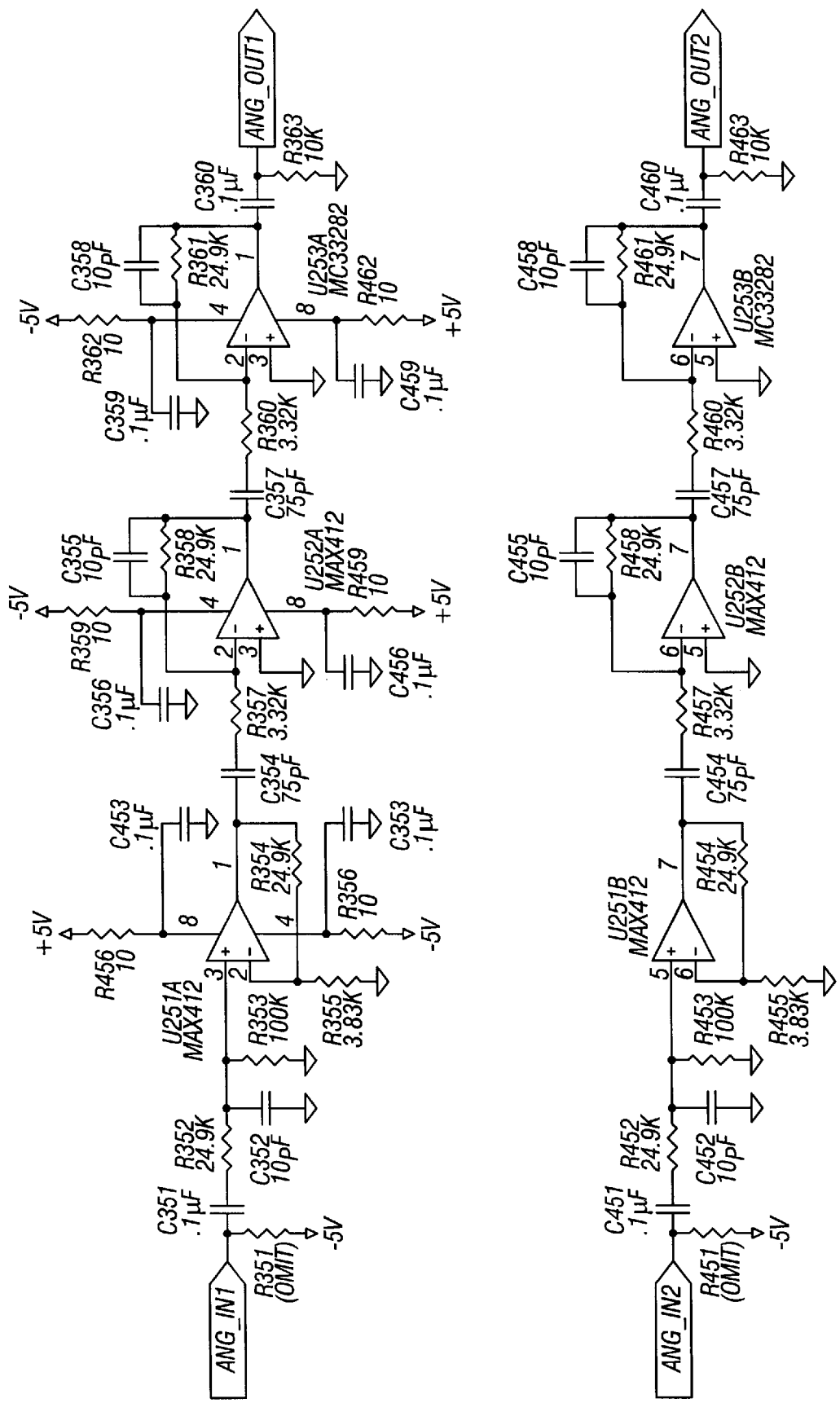
Figure 4H:
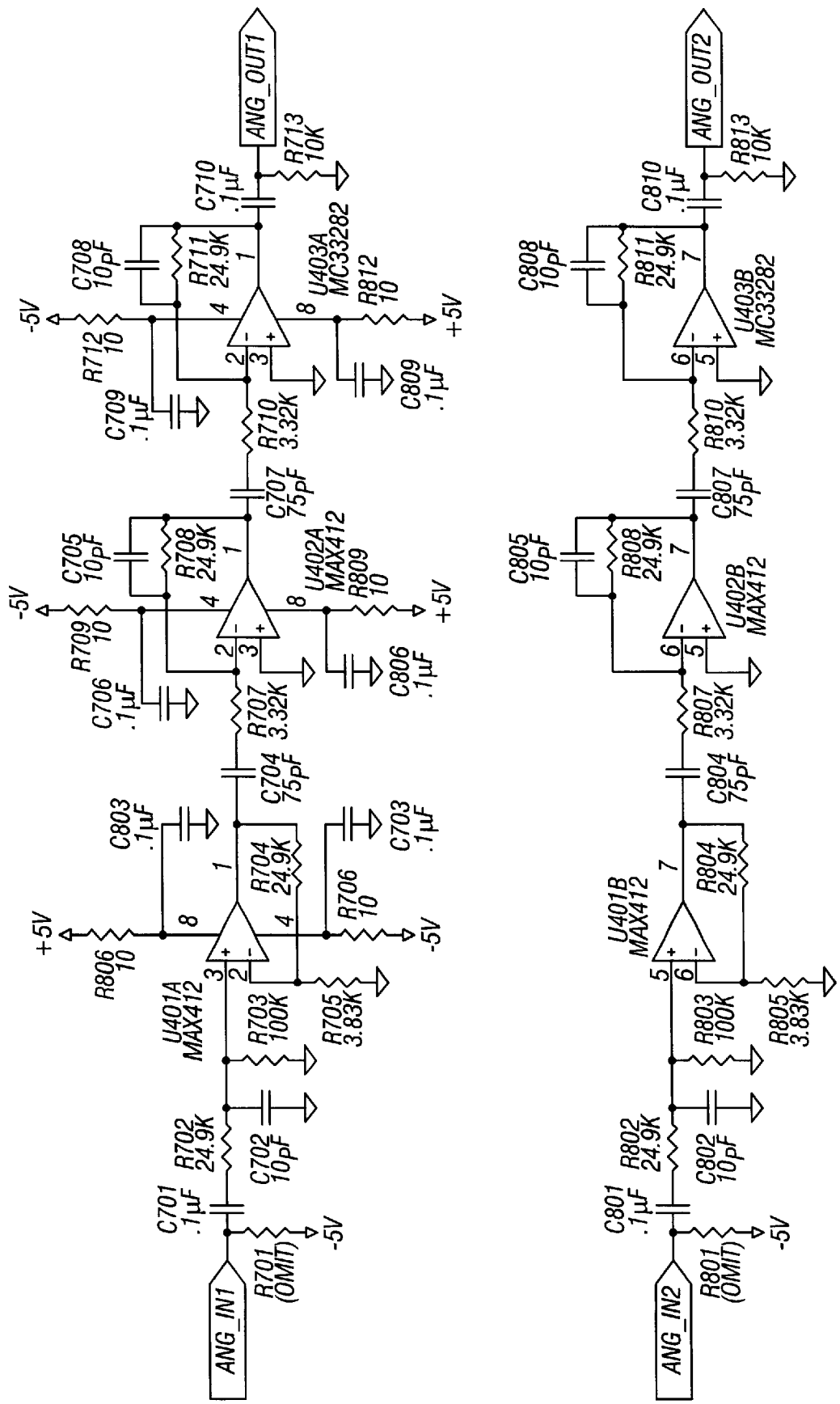
Figure 4I:
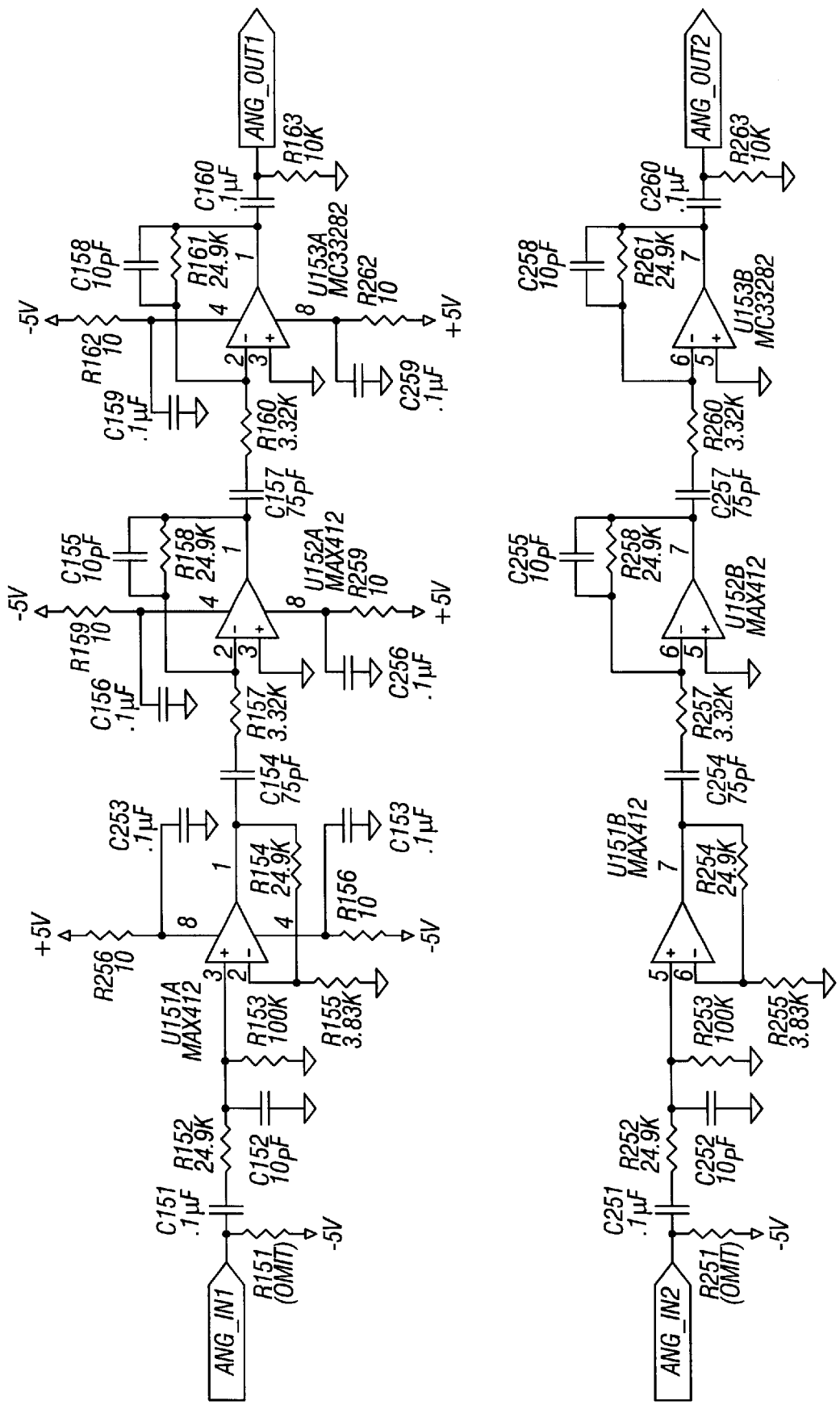

Referring next to FIG. 6, a block diagram is shown of functional components that make up one embodiment of a software system with which the computer of FIG. 2 is controlled.

Upon initialization (Block 100), the computer, under control of the software system, initializes (Block 102), and loads a default color map display (Block 104), which maps detected densities within the vehicle under inspection, i.e., pulse counts, to specific colors to be produced on the display device 38. Next, the user is presented with a main menu (Block 106), and the computer is instructed to wait until an operator instructs the software system as to what step to take next.

One of the options available to the operator is a help function (Block 108). The help function displays tutorial and/or reference information to the operator via the display device, as is common in the computing arts.

Another option presented to the operator is the "Display Image from Disk in Upper Window" option (Block 110). When selected this option allows the operator to load a saved display image from a hard or floppy disk drive within the computer, and to automatically display the image in the upper display window on the display drive. (See FIG. 8) Generally, the upper display window, in accordance with the present embodiment, is used to display a reference image, i.e., an image of the truck under inspection, but while empty, i.e., containing no contraband.

A further option that can be selected by the operator is a "Display Image from Disk in Lower Window" option (Block 112). When selected this option allows the operator to load a saved image from a hard or floppy disk drive within the computer, and automatically displays the image in the lower display window on the display drive. (See FIG. 8) Generally, the lower display window, in accordance with the present embodiment, is used to display an inspection image, i.e., an image of the vehicle under inspection. A useful function of this option is for reinspection of a vehicle at a later time by a supervisor in order to maintain quality control. Because the image is stored on disk, it is not necessary that the vehicle be present when this re-inspection takes place. The saved image of the vehicle, after being loaded, can easily be visually compared with the reference image loaded into the upper display window.

The next option available to the operator is the "Save Image from Lower Window to Disk" option. This option can be used to save an image of a vehicle under inspection for later reinspection, or can be used to save a reference image after a known empty vehicle has been inspected, i.e., scanned using the present embodiment.

Using a "Load Color Lookup Table from Disk" option (Block 116), the operator is able to load a previously saved color lookup table from disk. This allows the user to retrieve a color map, different from the default color map, so that a different set of colors can be mapped to various density measurements, i.e., pulse counts within the vehicle.

The next option is the "Acquire Image from Counters and Display to Screen" option (Block 118). This option initiates an image generation program, as described below in reference to FIG. 7, which causes the detector array 14 and the radiation source 18 to perform density measurements and causes the display of an image indicative of the various densities within the vehicle under inspection in the lower display window on the screen display. Advantageously, the present embodiment allows the operator to display a reference image in the upper display window while the inspection is being conducted, so that he or she can visually compare what the vehicle under inspection should look like empty with what the vehicle under inspection in fact looks like. In this way, the operator is able to determine whether or not the vehicle under inspection may contain contraband.

The next two options (Blocks 120 and 122) allow the operator to set values for what is referred to herein as the "K" constraint and the "L" constraint. These two "constraints" function in a manner similar to the well known functioning of the brightness and contrast controls on commonly available cathode ray tube-type displays. These values affect the mapping of colors to the various pulse counts, which is performed as follows:

(1) a "white" level, i.e., a number of counts corresponding to zero density, is determined for each sensor during detector calibration, which is a step in image acquisition as described below in reference to FIG. 7;

(2) the variable "T" is then set equal to this white level times the reciprocal of the number of photons counted by a particular detector at a particular horizontal position on the vehicle;

(3) If "T" is less than one, i.e., more photons are counted than the white level, then T is set equal to one;

(4) the variable "D" is then computed as follows: $D=254/(1+L)\ln(T*K)$, where L and K are the constraints mentioned above, which are initially set to one, and where T is defined above; and (5) If "D" is less than 1 or greater than 254, then D is set to 1 or 254, respectively.

The significance of the number 254 in the above computations is that there are 256 possible colors displayable on the preferred Super-VGA display device, however this number could be adjusted up or down to yield an appropriate color mapping where more or fewer colors are displayable.

Other options available to the user are options to "Redisplay Both Windows" (Block 124), "Redisplay the Upper Window" (Block 126) and "Redisplay the Lower Window" (Block 128). Redisplay options such as these are useful to the operator if the images displayed on the display device 38 become corrupted in some way, as for example may occur if text is sent to the display device 38 while it is displaying a graphical image.

The user may also "Reset a Default Color Map Array" (Block 130), "Load a Next Color Map Array" (Block 132) and "Load a Previous Color Map Array" (Block 134). These options are used to step through various preconfigured color maps, and to reestablish the default color map, so that the operator can utilize a color map that best emphasizes the features of the vehicle under inspection that he or she is inspecting.

Other options available to the user are to "Reset Modified Color Table" (Block 136), "Increase Color Table Gain" (Block 138), "Decrease Color Table Gain" (Block 140), "Increase Color Table Offset" (Block 142), and "Decrease Color Table Offset" (Block 144). These options affect the "mx+b" relationship between the photon counts determined by the gamma/x-ray detectors and the colors displayed on the display device. The "gain" (m) is initially set, or can be reset, to one, and the "offset" (b) is initially set, or can be reset, to zero. These two parameters allows the operator to "zoom" in on a particular range of densities for mapping within the color table by increasing or decreasing the offset in order to establish a minimum density of interest (with every density below this density being mapped to zero density (or "white"), and by increasing or decreasing the gain in order to establish a maximum density of interest (with every density above this density being mapped to maximum density (or "black").

A final operator-selectable option depicted in FIG. 6 is an "End" option (Block 146). This option is used by the operator to exit the software system and to return control to an operating system, such as is known in the art of computer technology.

As can be seen, various color maps, gains and offsets can be used to produce a variety of images representing densities detected within a vehicle during an inspection using the present embodiment.

Referring next to FIG. 7, a flow chart is shown of the steps traversed by the computer of FIG. 2 in response to the software system of FIG. 6 when an image generation program is executed.

Upon being initiated (Block 200), the image generation is initialized (Block 202), and the movement of the radiation source truck 20, and the detector array truck 16, if used, is initiated (Block 204). Next, the detectors 26 are calibrated (Block 206) by irradiating the detectors with the radiation source 18 at a point along the track before the radiation source truck 20 and the detector array truck 16 reach the vehicle to be inspected, i.e., before the vehicle under inspection is interposed between the detector array 16 and the radiation source 18. Such irradiation of the detectors 26 establishes a baseline of radiation (or "lwhite" photon count level) corresponding to a density in the vehicle being inspected of approximately zero and corresponding to a maximum photon count. Three photon counts are made in this manner for each detector 26. Such counts are then arranged for each detector 26 and then stored in an array having a white level element for each detector 26.

A horizontal position is then set to zero (Block 208). The horizontal position corresponds to a position along the track arbitrarily selected to be a first position at which density measurements are taken. This horizontal position should be at a point before the vehicle is interposed between the detector array 14 and the radiation source 18.

Next, a detector count is set to zero (Block 210), which corresponds to a first of the detectors 26 in the detector array 14 to be queried for a photon count. Next, this detector is queried for a photon count and is instructed to restart counting photons (Block 212). In response to this instruction, the detector queried restarts counting photons (Block 214) and the previously determined number of photon counts is passed along to the computer (Block 216). This number of photon counts is stored into an array within a memory in the computer (Block 218) and is then converted into a pixel value (Block 220). Conversion into the pixel value includes mapping the number of photon counts to a color to be displayed on the display device. Such mapping is described more completely above in reference to FIG. 6. Next, the detector number queried is converted into a vertical position on the screen display (Block 202) and the horizontal position of the radiation source truck 20 and the detector array truck 16 along the tracks is converted to a horizontal position on the screen display. Next, the pixel at the determined horizontal and vertical positions is illuminated using the color corresponding to the number of photon counts, as previously converted (Block 224).

Next, a determination is made as to whether all of the detectors 26 in the detector array 14 have been queried for a number of photon counts for the current horizontal position (Block 226). If all the detectors have not been queried (Block 226), the detector number to be queried is incremented (Block 227) and execution of the image generation program continues by querying the next detector in the detector array 14 for the number of photon counts, and by instructing such detector to restart counting (Block 212). Execution continues from this point as described above (Block 214 et seq.) If all the detectors within the detector array 14 have been queried for the current horizontal position (Block 226), the horizontal position is incremented (Block 228) and a determination is made as to whether or not the radiation source truck 20 and the detector array truck 16 are still moving (Block 230). If the radiation source truck 20 and the detector array truck 16 are still moving (Block 230), the detector to be queried is reset to zero (Block 210) and execution of the image generation program continues as described above (Block 212 et seq.).

If the radiation source truck 20 and the detector array truck 16 have stopped moving (because they have reached the farthest point of travel down the tracks (Block 230)), execution of the image generation program is terminated (Block 232).

Referring next to FIG. 8, a diagram is shown illustrating a preferred screen layout for the images displayed on the display device of FIG. 2.

As shown, the screen display 300 is divided into an upper display 302, a lower display 304 and a color bar 306. In accordance with the present embodiment, the upper display 302 can be used, as mentioned above, to display images stored on disk. These images will generally be reference images used for visual comparison with an image representative of a vehicle under inspection. The lower display 304, in addition to being able to display images stored on disk, is used to display images, as they are generated, indicative of the various densities within the vehicle under inspection. Both the upper and lower displays 302, 304 are color mapped using the current color map, gain and offset, so that they can be visually compared to one another.

Any differences in a reference image, and an image generated during inspection of a vehicle may indicate the presence of contraband within the vehicle under inspection.

The color bar 306 indicates the colors that are mapped to the various densities detectable by the present embodiment, serving as a reference to the operator as to which colors indicate higher densities than others. As suggested in FIG. 8, colors nearer to the top of the color bar 306 are indicative of more density, i.e., fewer photons counted as penetrating the vehicle under inspection, and colors nearer to the bottom of the color bar 306 are indicative of less density, i.e., more photons counted as penetrating the vehicle under inspection.

Thus, a system and associated methods are provided in the present embodiment for determining the densities within a vehicle under inspection based on discrete photon counting, and for generating an image indicative of such densities. Advantageously, such determination is made based on discrete photon counting, thereby eliminating the need for high levels of gamma-ray or x-ray radiation.

The present embodiment, thus, eliminates the need to stop and manually inspect vehicles at border crossings, and other inspection points. In addition, the present embodiment advantageously eliminates the need to stop and evacuate the vehicle before it is subjected to very high strength gamma-ray or x-ray radiation. Advantageously, one variation the present embodiment provides for the determination of densities within the vehicle without the need even to stop the vehicle. Slightly higher radiation levels may, in accordance with this variation, be used to reduce or even eliminate the slowing needed to determine the densities within a vehicle, and to generate an image indicative thereof.

While the invention herein disclosed has been described by means of specific embodiments and applications thereof, numerous modifications and variations could be made thereto by those skilled in the art without departing from the scope of the invention set forth in the claims.

What is claimed is:

1. A system for measuring relative densities of materials contained within a target object comprising:
    a radiation source for radiation photons toward the target object;
    an array of photon detectors coupled to the radiation source for receiving photons passing through the target object;
    moving means for moving the radiation source and the array of photon detectors in parallel along a first and second track straddling the target object so as to maintain a constant distance between the radiation source and the array of photon detectors;
    a discriminator coupled to the array of photon detectors for generating a pulse only in response to a waveform corresponding to a received photon that exceeds a selected noise threshold; and
    a counter coupled to the discriminator.

2. The system of claim 1 further comprising a display device coupled to the counter for displaying relative densities of materials contained within the target object.

3. The system of claim 1 wherein the display device comprises mapping means for mapping a counted number of pulses for each photon detector to a color.

4. The system of claim 1 wherein the display device comprises mapping means for mapping a counted number of pulses for each photon detector to a gray-scale.

5. A method of measuring relative densities within a target object comprising the steps of:
    irradiating the target object, the target object being selected from the group consisting of a vehicle, a cargo container, and a railroad car;
    detecting a first discrete number of photons penetrating the target object through a first prescribed volume and entering a first radiation detector;
    detecting a second discrete number of photons penetrating the target object through a second prescribed volume and entering a second radiation detector;
    discriminating an amplified output of the first radiation detector with a discriminator to generate a first number of pulses only in response to waveforms in the amplified output of the first radiation detector that exceed a selected noise threshold;
    counting the second number of pulses with a counter;
    displaying a graphical representation of relative densities (D) within the first volume of the target object in response to the first number of pulses and within the second volume of the target object in response to the second number of pulses;
    mapping the first number of pulses to a first color; and
    mapping the second number of pulses to a second color, wherein the mapping is performed for each of the first and second radiation detectors according to a relationship between a first, second, and third constraint, wherein the first constraint corresponds to contrast, the second constraint corresponds to brightness, and the third constraint corresponds to a white level or zero density times the reciprocal number of photons counted by a detector of the detector array at a particular position on the target object.

6. The method of claim 5 wherein the step of displaying includes mapping the first number of pulses to a first shade of gray and mapping the second number of pulses to a second shade of gray.

7. A system for measuring relative densities within a target object comprising:
    a source platform;
    a detector platform;
    a radiation source positioned on the source platform;
    a detector array positioned on the detector platform wherein the detector array comprises a plurality of photon detectors;
    a motor coupled to the source platform and the detector platform for moving the source platform and the detector platform so as to maintain a constant distance therebetween to scan at least a portion of the target object, wherein the motor moves the source platform and the detector platform in parallel along a first and second track straddling the target object;
    a discriminator coupled to the detector array for generating a pulse only in response to a waveform corresponding to a received portion that exceeds a selected noise threshold; and
    a counter coupled to the discriminator.

8. The system of claim 7 further comprising a display device coupled to the counter for displaying relative densities of materials contained within the target object.

9. The system of claim 7 wherein the radiation source generates gamma radiation having an energy of about 662 keV.

10. The system of claim 7 wherein the radiation source generates radiation at an intensity of about $3.7 \times 10^{10}$ Bq.

11. The system according to claim 7, wherein the source platform and the detector platform are moved at a constant speed.

12. The system according to claim 7, wherein the source platform and the detector platform are moved at a predetermined counting interval so as to effect a predetermined longitudinal pixel length.

13. The system according to claim 12, wherein the predetermined pixel length is approximately 2.5 cm to 5.0 cm.

14. The system according to claim 12, further including a variable frequency generator for controlling the speed of the motor.

15. A system for measuring relative densities of materials contained within a target object comprising:
- a radiation source for directing radiation toward the target object, the target object being selected from the group consisting of a vehicle, a cargo container, and a railroad car;
- a detector array coupled to the radiation source for receiving radiation passing through the target object;
- a discriminator coupled to the detector array for generating a pulse only in response to each waveform corresponding to a received photon that exceeds a selected noise threshold; and
- a display device coupled to the discriminator for displaying relative densities of materials contained within the target object, wherein the display device includes means for retrieving a stored display and means for concurrently displaying the stored display and the relative densities of materials contained within the target object, wherein the relative densities for each detector in the detector array are displayed according to a relationship between a first, second, and third constraint, wherein the first constraint corresponds to contrast, the second constraint corresponds to brightness, and the third constraint corresponds to a white level or zero density times the reciprocal number of photons counted by a detector of the detector array at a particular position on the target object.

16. The system of claim 15 wherein the radiation source is a gamma radiation source.

17. The system of claim 15 further comprising a shutter coupled to the gamma radiation source.

18. The system of claim 15 wherein the radiation source generates gamma radiation having an energy of about 662 keV.

19. The system of claim 15 wherein the radiation source has an intensity of about $3.7 \times 10^{10}$ Bq.

20. The system of claim 15 further comprising a motion controller for maintaining a substantially constant distance between the radiation source and the detector array.

* * * * *